(12) United States Patent
Mandelkow et al.

(10) Patent No.: US 8,410,152 B2
(45) Date of Patent: Apr. 2, 2013

(54) THIAZOLHYDRAZIDES FOR TREATMENT OF NEURODEGENERATIVE DISEASES

(75) Inventors: Eckhard Mandelkow, Hamburg (DE); Eva-Maria Mandelkow, Hamburg (DE); Markus Pickhardt, Hamburg (DE); Jacek Biernat, Schenefeld (DE); David George Lloyd, Malahide (IE); Boris Schmidt, Darmstadt (DE); Gregor Larbig, Gelnhausen (DE)

(73) Assignees: Max-Planck-Gesellschaft zur Forderung der Wissenschaften e. V., Munich (DE); Technische Universitat Darmstadt, Damstadt (DE); The Provost Fellows and Scholars of the College of the Holy and Undivided Trinity of Queen Elizabeth near Dublin, Dublin 2 (IE)

(*) Notice: Subject to any disclaimer, the term of this patent is extended or adjusted under 35 U.S.C. 154(b) by 374 days.

(21) Appl. No.: 12/513,480

(22) PCT Filed: Nov. 5, 2007

(86) PCT No.: PCT/EP2007/009563
§ 371 (c)(1),
(2), (4) Date: Feb. 23, 2010

(87) PCT Pub. No.: WO2008/052804
PCT Pub. Date: May 8, 2008

(65) Prior Publication Data
US 2010/0151064 A1    Jun. 17, 2010

(30) Foreign Application Priority Data
Nov. 5, 2006    (EP) .................... 06022992

(51) Int. Cl.
*A01N 43/78* (2006.01)
*A61K 31/425* (2006.01)

(52) U.S. Cl. ........ 514/370; 514/367; 514/394; 548/150; 548/190; 548/304.7; 564/148; 549/399

(58) Field of Classification Search ................ 514/370, 514/367; 548/150, 190; 564/148; 549/399
See application file for complete search history.

(56) References Cited

U.S. PATENT DOCUMENTS

| | | | |
|---|---|---|---|
| 6,069,162 | A | 5/2000 | Itoh et al. |
| 7,087,628 | B2 | 8/2006 | Sui et al. |
| 7,244,842 | B2 | 7/2007 | Desphande et al. |
| 2004/0132788 | A1 | 7/2004 | De Lassauniere et al. |
| 2004/0152747 | A1 | 8/2004 | Chen et al. |
| 2007/0054900 | A1 | 3/2007 | De Lassauniere et al. |
| 2009/0198066 | A1 | 8/2009 | Parthasaradhi Reddy et al. |

OTHER PUBLICATIONS

Mangialasche et al. (LancetNeurol. 2010; 9: p. 702-716).*

(Continued)

*Primary Examiner* — Noble Jarrell
*Assistant Examiner* — Valerie Rodriguez-Garcia
(74) *Attorney, Agent, or Firm* — Meyertons, Hood, Kivlin, Kowert & Goetzel, P.C.; Eric B. Meyertons

(57) ABSTRACT

Described are compounds having a thiazolhydrazide scaffold, pharmaceutically acceptable salts of these compounds and pharmaceutical compositions containing at least one of these compounds together with pharmaceutically acceptable carrier, excipient and/or diluents. Said thiazolhydrazide compounds can be used for prophylaxis and/or treatment of neurodegenerative diseases and conditions.

6 Claims, 1 Drawing Sheet

OTHER PUBLICATIONS

Souillac et al., Characterization of Delivery Systems, Differential Scanning Calorimetry, (in Encyclopedia of Controlled Drug Delivery, 1999, John Wiley & Sons, pp. 212-227).*
Morissette et al. Advanced Drug Delivery Reviews 2004, 56, 275-300).*
Vippagunta et al. Advanced Drug Delivery Reviews 2001, 48, 3-26).*
(Wolff, Manfred E. "Burger's Medicinal Chemistry, 5ed, Part I", John Wiley & Sons, 1995, pp. 975-977.*
Banker et al, "Modern Pharmaceutics, 3ed.", Marcel Dekker, New York, 1996, pp. 451 and 596.*
Jordan, V. C. Nature Reviews: Drug Discovery, 2, 2003, pp. 205-213.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Schirmer et al. (Neurobiology of Aging, (2011), 32: p. 2325.e7-2325.e16).*
Morris et al. "The Many Faces of Tau" Neuron 70, May 12, 2011, pp. 410-426.

* cited by examiner

Compound 8 = BSc3094

THIAZOLHYDRAZIDES FOR TREATMENT OF NEURODEGENERATIVE DISEASES

BACKGROUND OF THE INVENTION

1. Field of the Invention

The present invention generally relates to thiazolhydrazide derivatives and stereoisomeric forms, prodrugs, solvates, hydrates and/or pharmaceutically acceptable salts of these compounds as well as pharmaceutical compositions containing at least one of these thiazolhydrazides derivatives together with pharmaceutically acceptable carrier, excipient and/or diluents. Said thiazolhydrazides derivatives have been identified as specific inhibitors of aggregation of Tau-proteins and are useful for the treatment of Alzheimer's Disease and related neurodegenerative diseases, disorders and conditions.

2. Description of the Relevant Art

Tauopathies belong to the group of neurodegenerative diseases in which accumulation of Tau-protein in the brain is observed. Diseases like Alzheimer Disease, Morbus Pick and Corticobasal Degeneration are well known diseases belonging to this group, wherein the most investigated disease of this group is Alzheimer Disease.

Alzheimer's is the most common form of dementia that gradually destroys brain cells and leads to progressive decline in mental function. This pathological process consists principally of neuronal loss or atrophy mainly in the temporoparietal cortex, but also in the frontal cortex, together with an inflammatory response to the deposition of amyloid plaques and neurofibrillary tangles.

Morbus Pick (Frontotemporal Dementia, FTD, Pick's Disease) is a relatively rarely occurring demential disorder having a prevelence of ca. 2% among all patients suffering from mental disorders. As the name (FTD) suggests Pick's Disease is associated with shrinking of the frontal and temporal anterior lobes of the brain leading to massive change in behaviour and problems with language.

Corticobasal Degeneration is a progressive neurological disorder characterized by nerve cell loss and atrophy of multiple areas of the brain including the cerebral cortex and the basal ganglia.

The use of phenylthiazoles for treating neurodegenerative diseases has been described earlier. WO 2005/035510 A1 and EP 1 223 933 B1 both disclose phenylthiazoles for treatment of Alzheimer's disease and Parkinson's disease.

WO 98/27108 A2 discloses 4-phenylthiazole for treatment of NO-mediated diseases and for Alzheimer Disease.

EP 1 448 553 B1 discloses N-substituted heterocyclic hydrazides having neurotrophic activity for treatment of diseases like Parkinson's Disease, Alzheimer Disease, stroke and multiple sclerosis.

None of these prior art documents disclose the use of the claimed thiazolhydrazides derived compounds described in the present application for the treatment of neurodegenerative diseases.

SUMMARY OF THE INVENTION

Described herein are compounds and/or pharmaceutically acceptable salts thereof which can be used as pharmaceutically active agents, especially for the treatment of neurodegenerative diseases as well as compositions including at least one of those compounds and/or pharmaceutically acceptable salts thereof as pharmaceutically active ingredients.

The problems described above are solved by the teaching of the independent claims. Further advantageous features, aspects and details of the invention are evident from the dependent claims, the description, and the examples of the present application.

The novel thiazolhydrazide derivatives according to one embodiment are represented by the following general formula (I):

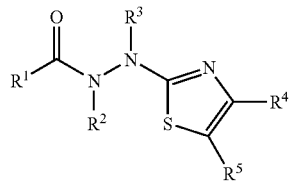

wherein $R^1$ represents —$R^6$, —$CR^6R^7R^8$, —X—$CR^9R^{10}R^{11}$, —X—$R^6$, —X—$R^{6O4}$;

$R^4$ represents —H, —$R^7$, —Y—$R^7$, —$CR^{12}R^{13}R^{14}$, —Y—$CR^{12}R^{13}R^{14}$;

$R^5$ represents —H, —$R^8$, —Z—$R^8$, —$CR^{15}R^{16}R^{17}$, —Z—$CR^{15}R^{16}R^{17}$;

$R^4$ and $R^5$ represent the following ring system

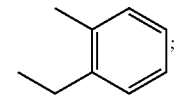

X, Y, Z can be selected independently from —$(CH_2)_n$—, —O—, —S—, —NH—, —CH=CH—, —C≡C—, —O—$(CH_2)_m$—, —NH—$(CH_2)_p$—, para-$C_6H_4$;

Y, Z can be selected independently from —CO—, —CO—O—, —O—CO—, —NH—CO—, —CO—NH—;

n, m and p represent independently from each other an integer from 1 to 6;

$R^6$, $R^7$, $R^8$ represent —$CH_3$, —$CF_3$, —F, —Cl,

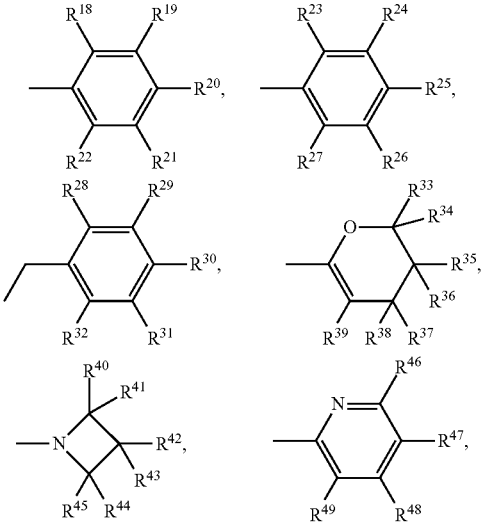

-continued
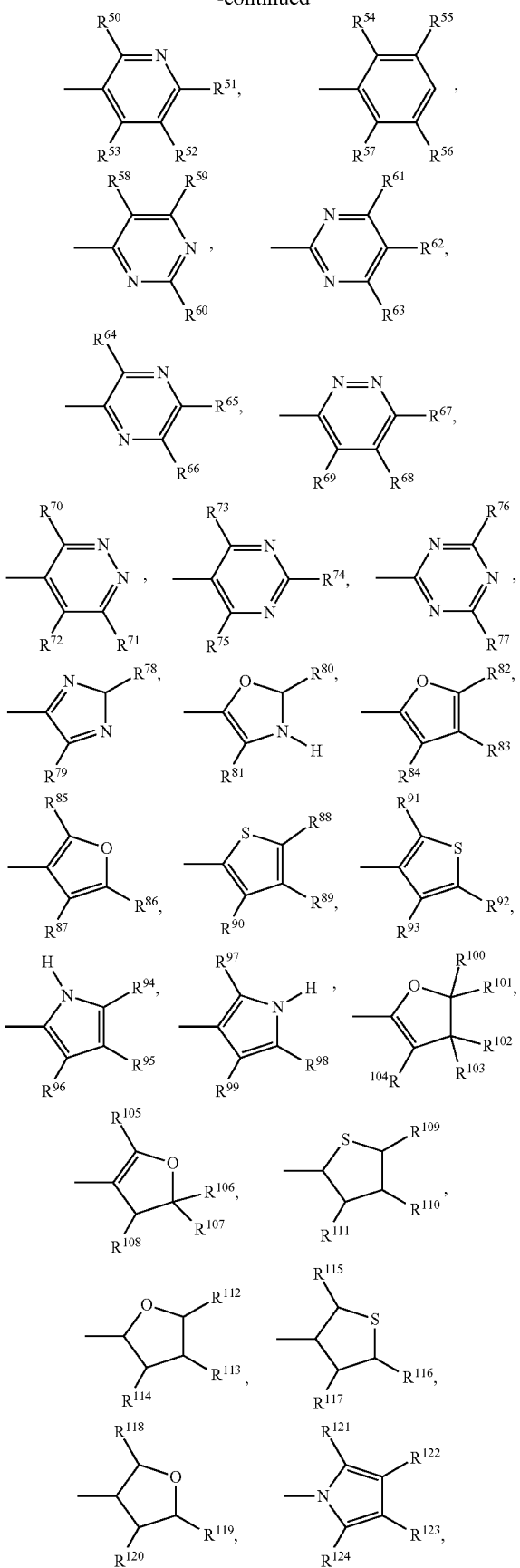
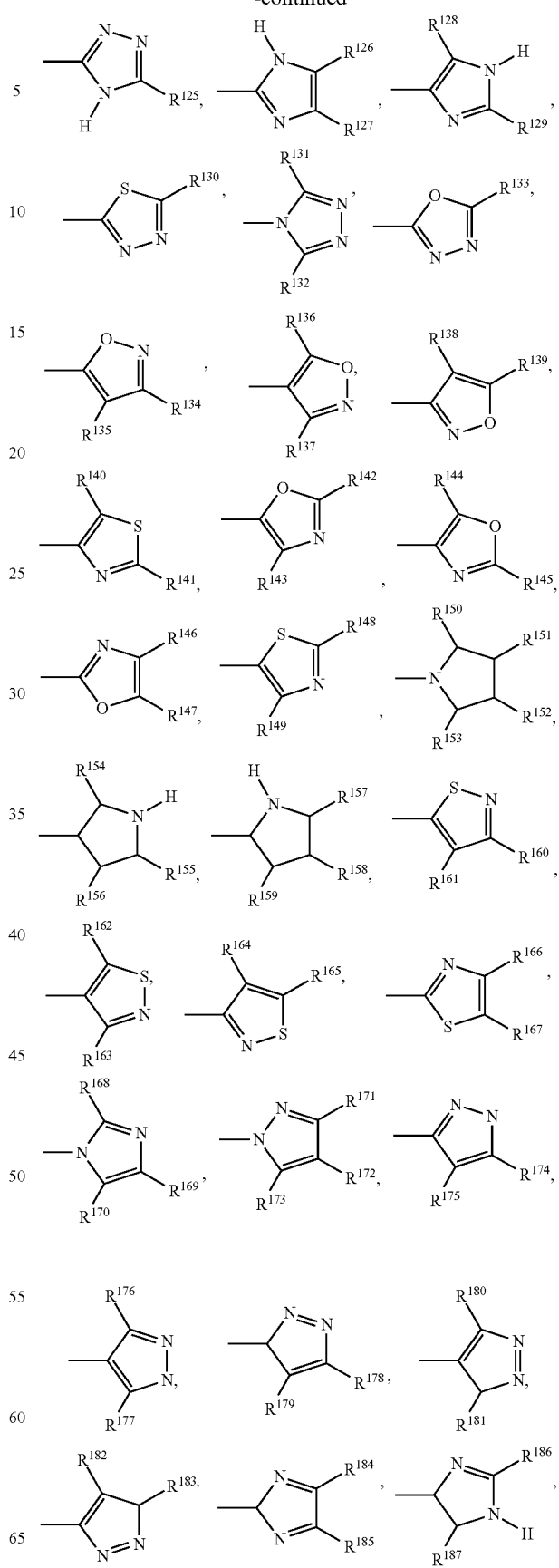

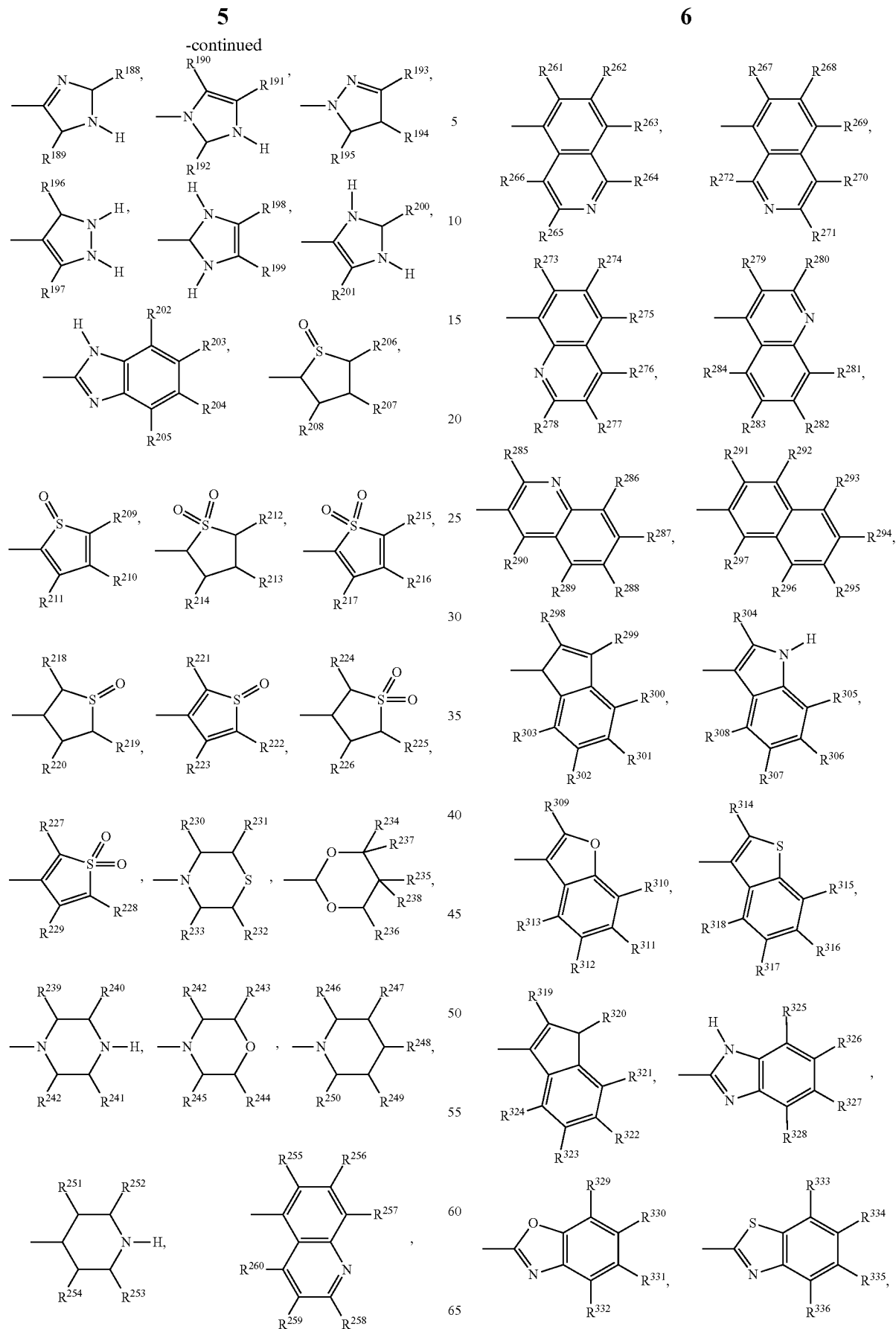

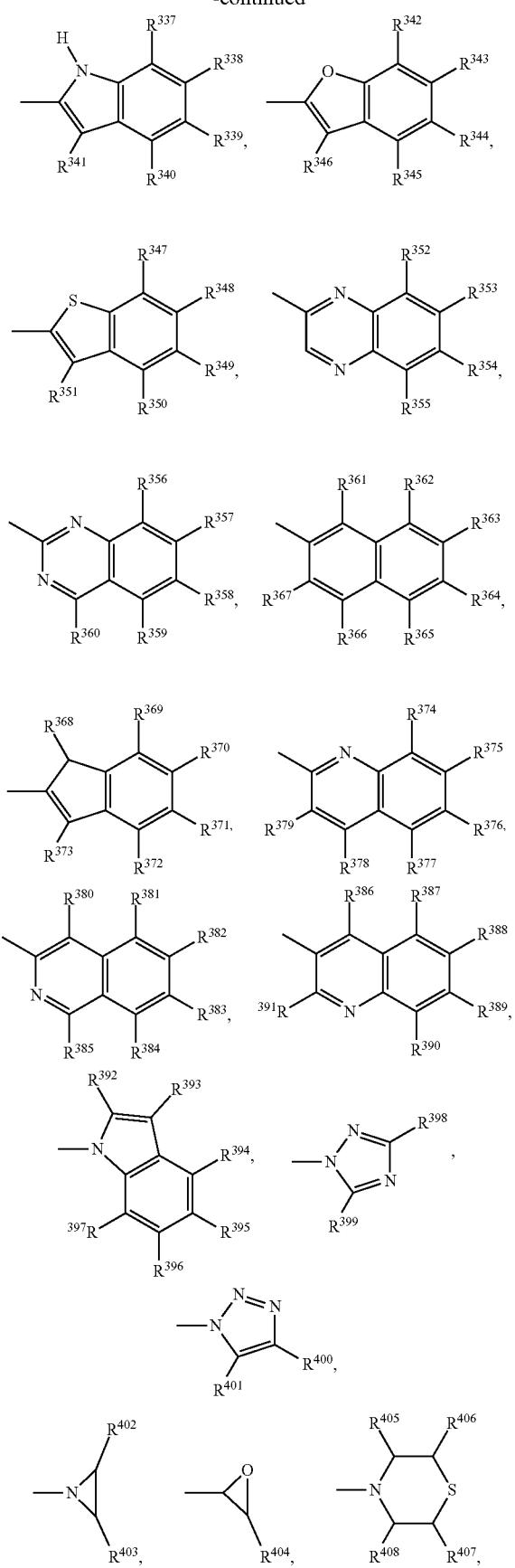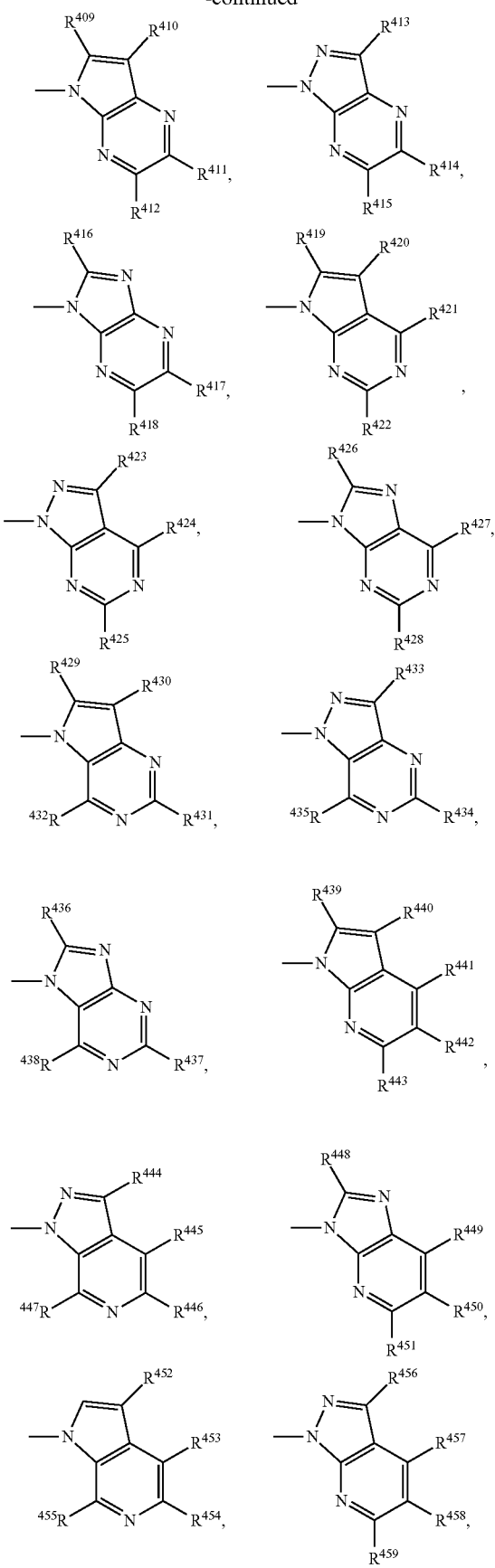

-continued
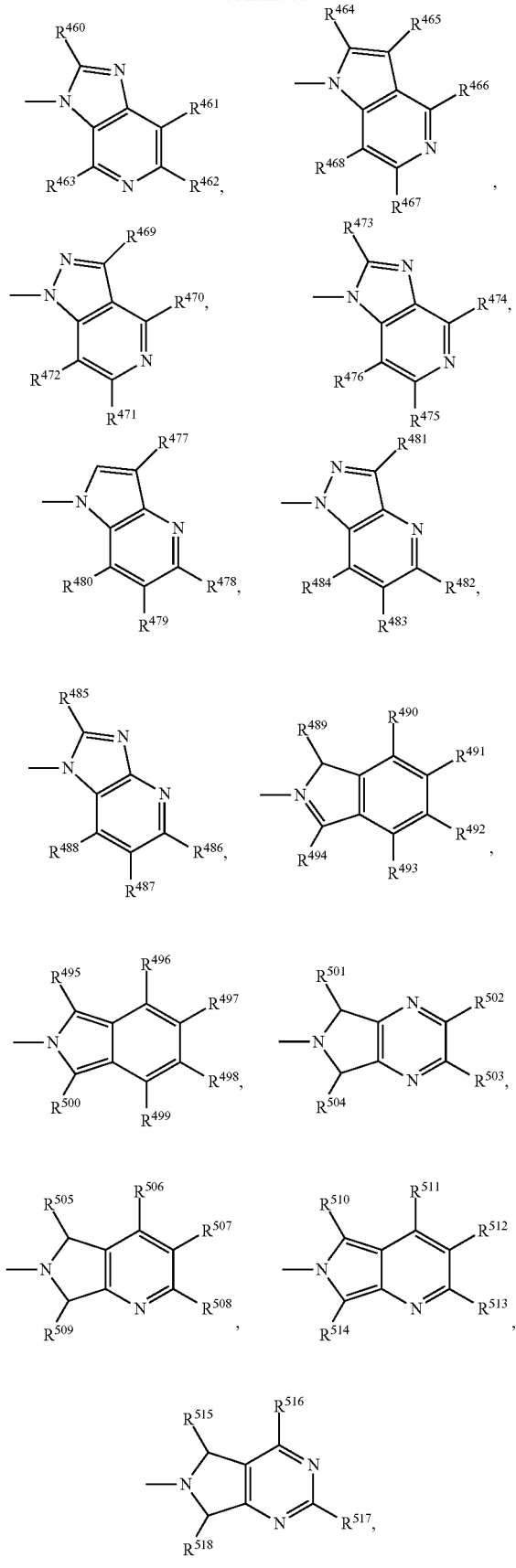
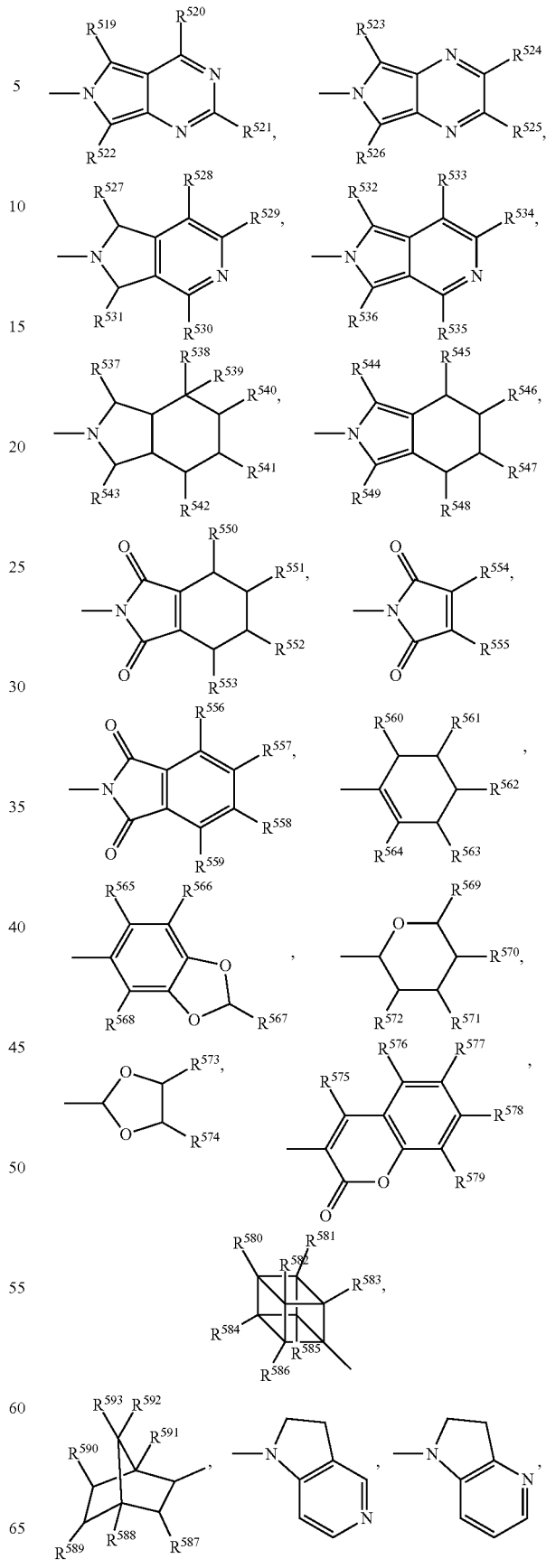

-continued

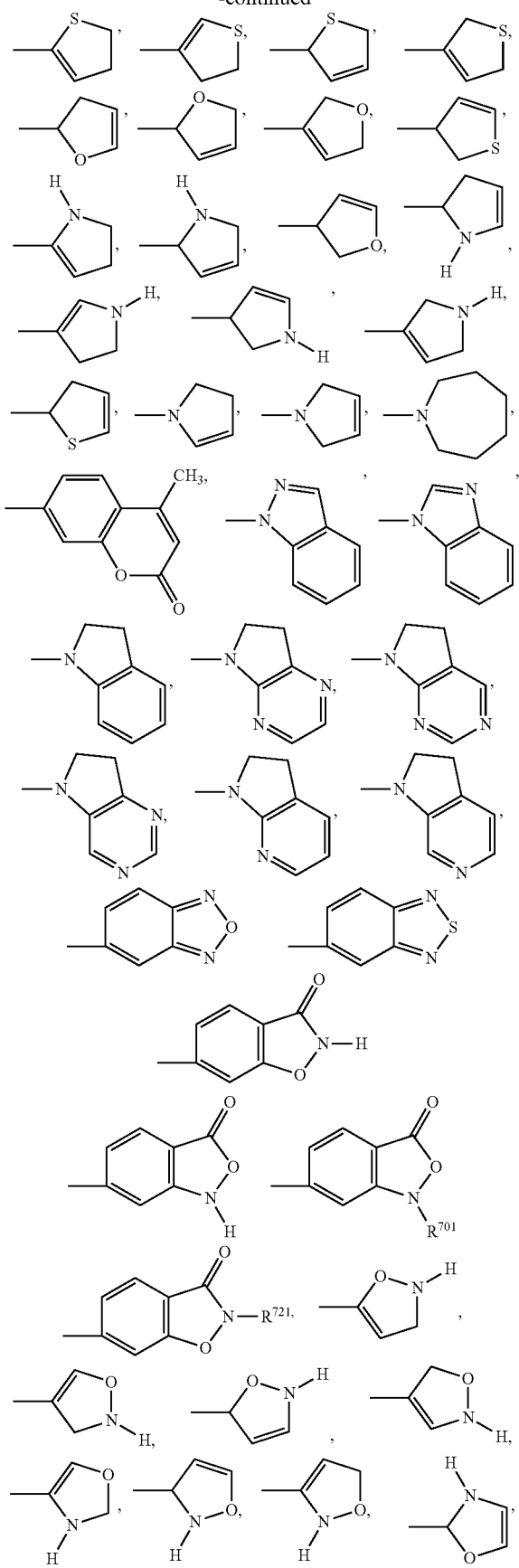
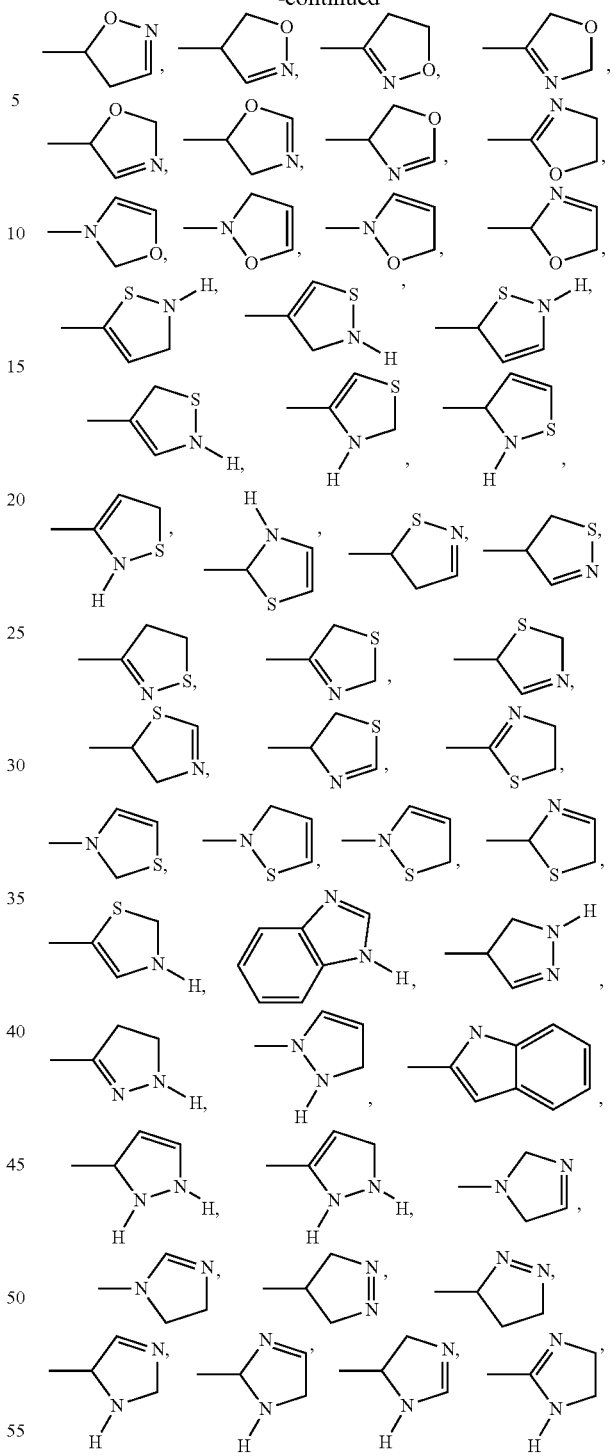

$R^9$-$R^{593}$ can be selected independently from —$R^{604}$ to —$R^{1198}$, —H, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OPh, —OCH$_2$-Ph, —OCPh$_3$, —SH, —SCH$_3$, —SC$_2$H$_5$, —SC$_3$H$_7$, —S-cyclo-C$_3$H$_5$, —SCH(CH$_3$)$_2$, —SC(CH$_3$)$_3$, —NO$_2$, —F, —Cl, —Br, —I, —N$_3$, —CN, —OCN, —NCO, —SCN, —NCS, —CHO, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, —COCN, —COOCH$_3$, —COOC$_2$H$_5$, —COOC$_3$H$_7$, —COO-cyclo- —C₃H₅, —COOCH(CH₃)₂, —COOC(CH₃)₃, —OOC—CH₃, —OOC—C₂H₅, —OOC—C₃H₇, —OOC-cyclo-C₃H₅, —OOC—CH(CH₃)₂, —OOC—C(CH₃)₃, —CONH₂, —CONHCH₃, —CONHC₂H₅, —CONHC₃H₇, —CONH-cyclo-C₃H₅, —CONH[CH(CH₃)₂], —CONH[C(CH₃)₃], —CON(CH₃)₂, —CON(C₂H₅)₂, —CON(C₃H₇)₂, —CON(cyclo-C₃H₅)₂, —CON[CH(CH₃)₂]₂, —CON[C(CH₃)₃]₂, —NHCOCH₃, —NHCOC₂H₅, —NHCOC₃H₇, —NHCO-cyclo-C₃H₅, —NHCO—CH(CH₃)₂, —NHCO—C(CH₃)₃, —NHCO—OCH₃, —NHCO—OC₂H₅, —NHCO—OC₃H₇, —NHCO—O-cyclo-C₃H₅, —NHCO—OCH(CH₃)₂, —NHCO—OC(CH₃)₃, —NH₂, —NHCH₃, —NHC₂H₅, —NHC₃H₇, —NH-cyclo-C₃H₅, —NHCH(CH₃)₂, —NHC(CH₃)₃, —N(CH₃)₂, —N(C₂H₅)₂, —N(C₃H₇)₂, —N(cyclo-C₃H₅)₂, —N[CH(CH₃)₂]₂, —N[C(CH₃)₃]₂, —SOCH₃, —SOC₂H₅, —SOC₃H₇, —SO-cyclo-C₃H₅, —SOCH(CH₃)₂, —SOC(CH₃)₃, —SO₂CH₃, —SO₂C₂H₅, —SO₂C₃H₇, —SO₂-cyclo-C₃H₅, —SO₂CH(CH₃)₂, —SO₂C(CH₃)₃, —SO₃H, —SO₃CH₃, —SO₃C₂H₅, —SO₃C₃H₇, —SO₃-cyclo-C₃H₅, —SO₃CH(CH₃)₂, —SO₃C(CH₃)₃, —SO₂NH₂, —OCF₃, —OC₂F₅, —O—COOCH₃, —O—COOC₂H₅, —O—COOC₃H₇, —O—COO-cyclo-C₃H₅, —O—COOCH(CH₃)₂, —O—COOC(CH₃)₃, —NH—CO—NH₂, —NH—CO—NHCH₃, —NH—CO—NHC₂H₅, —NH—CO—NHC₃H₇, —NH—CO—NH-cyclo-C₃H₅, —N—H—CO—NH[CH(CH₃)₂], —N—H—CO—NH[C(CH₃)₃], —N—H—CO—N(CH₃)₂, —NH—CO—N(C₂H₅)₂, —NH—CO—N(C₃H₇)₂, —NH—CO—N(cyclo-C₃H₅)₂, —NH—CO—N[CH(CH₃)₂]₂, —NH—CO—N[C(CH₃)₃]₂, —NH—CS—N—H₂, —NH—CS—NHCH₃, —N—H—CS—NHC₂H₅, —N—H—CS—NHC₃H₇, —N—H—CS—N—H-cyclo-C₃H₅, —N—H—CS—NH[CH(CH₃)₂], —NH—CS—NH[C(CH₃)₃], —NH—CS—N(CH₃)₂, —N—H—CS—N(C₂H₅)₂, —NH—CS—N(C₃H₇)₂, —NH—CS—N(cyclo-C₃H₅)₂, —N—H—CS—N[CH(CH₃)₂]₂, —NH—CS—N[C(CH₃)₃]₂, —NH—C(=NH)—NH₂, —NH—C(=NH)—NHCH₃, —NH—C(=NH)—NHC₂H₅, —NH—C(=NH)—NHC₃H₇, —NH—C(=NH)—NH-cyclo-C₃H₅, —N—H—C(=N—H)—NH[CH(CH₃)₂], —NH—C(=NH)—NH[C(CH₃)₃], —NH—C(=NH)—N(CH₃)₂, —NH—C(=NH)—N(C₂H₅)₂, —NH—C(=NH)—N(C₃H₇)₂, —NH—C(=NH)—N(cyclo-C₃H₅)₂, —N—H—C(=N—H)—N[CH(CH₃)₂]₂, —NH—C(=NH)—N[C(CH₃)₃]₂, —O—CO—NH₂, —O—CO—NHCH₃, —O—CO—NHC₂H₅, —O—CO—NHC₃H₇, —O—CO—N—H-cyclo-C₃H₅, —O—CO—NH[CH(CH₃)₂], —O—CO—NH[C(CH₃)₃], —O—CO—N(CH₃)₂, —O—CO—N(C₂H₅)₂, —O—CO—N(C₃H₇)₂, —O—CO—N(cyclo-C₃H₅)₂, —O—CO—N[CH(CH₃)₂]₂, —O—CO—N[C(CH₃)₃]₂, —O—CO—OCH₃, —O—CO—OC₂H₅, —O—CO—OC₃H₇, —O—CO—O-cyclo-C₃H₅, —O—CO—OCH(CH₃)₂, —O—CO—OC(CH₃)₃;

$R^2$, $R^3$, $R^{604}$-$R^{1198}$ represent

—H, —CH₃, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, cyclo-C₃H₅, cyclo-C₄H₇, cyclo-C₅H₉, cyclo-C₆H₁₁, cyclo-C₇H₁₃, cyclo-C₈H₁₅, -Ph, —CH₂-Ph, —CPh₃, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₇H₁₅, —C₈H₁₇, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH=CH₂, —C(CH₃)=CH₂, —CH=CH—CH₃, —C₂H₄—CH=CF₁₂, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—CH=CH—C(CH₃)=CF₁₂, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH=C—C₂H₅, —CH=CH—C₃H₇, —CH₂—CH=CH—CH=CH₂, —CH=CH—CH=CH—CH₃, —CH=CH—CH₂—CH=CH₂, —C(CH₃)=CH—CH=CH₂, —CH=C(CH₃)—CH=CH₂, —CH=CH—C(CH₃)=CH₂, —CH=CH—CH=CH—CH₃, —C(CH₃)=CH—C₂H₅, —C(CH₃)=CH—C₂H₅, —C(CH₃)=C(CH₃)₂, —C(CH₃)₂—CH=CH₂, —CH(CH₃)—C(CH₃)=CH₂, —C(CH₃)—CH=CH—CH₃, —CH=C(CH₃)—CH=CH₂, —CH₂—CH(CH₃)=CH₂, —C₄H₈—CH=CH₂, —C₃H₆—CH=CH—CH₃, —C₂H₄—CH=CH—C₂H₅, —CH₂—CH=CH—C₃H₇, —CH=CH—C₄H₉, —C₃H₆—C(CH₃)=CH₂, —C₂H₄—CH(CH₃)—CH=CH₂, —CH₂—CH(CH₃)—CH₂—CH=CH₂, —C₂H₄—CH=C(CH₃)₂, —CH(CH₃)—C₂H₄—CH=CH₂, —C₂H₄—C(CH₃)=CH—CH₃, —CH₂—CH(CH₃)—CH=CH—CH₃, —CH(CH₃)—CH₂—CH=CH—CH₃, —CH₂—CH=CH—CH(CH₃)₂, —CH₂—CH=C(CH₃)—C₂H₅, —CH₂—C(CH₃)=CH—C₂H₅, —CH(CH₃)—CH=CH—C₂H₅, —CH=CH—CH₂—CH(CH₃)₂, —CH=CH—CH(CH₃)—C₂H₅, —CH=C(CH₃)—C₃H₇, —C(CH₃)=CH—C₃H₇, —CH₂—CH(CH₃)—C(CH₃)=CH₂, —C[C(CH₃)₃]=CH₂, —CH(CH₃)—CH₂—C(CH₃)=CH₂, —CH(CH₃)—CH(CH₃)—CH=CH₂, —CH=CH—C₂H₄—CH=CH₂, —C(CH₃)₂—CH=CH—CH₃, —CH₂—C(CH₃)₂—CH=CH₂, —C(CH₃)₂—CH₂—CH=CH₂, —CH(CH₃)—CH=C(CH₃)₂, —CH₂—C(CH₃)=C(CH₃)₂, —CH=CH—CH₂—CH=CH—CH₃, —CH(CH₃)—C(CH₃)=CH—CH₃, —CH=C(CH₃)—CH(CH₃)₂, —C(CH₃)=CH—CH CH(CH₃)₂, —C(CH₃)=C(CH₃)—C₂H₅, —CH=CH—C(CH₃)₃, —C(CH₃)₂—CH=CH₂, —C(CH₃)₂—C(CH₃)=CH₂, —CH(C₂H₅)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[CH(CH₃)(C₂H₅)]=CF₁₂, —C[CH₂—CH(CH₃)₂]=CH₂, —C₂H₄—CH=CH—CH=CH₂, —CH₂—CH=CH—CH₂—CH=CH₂, —C₃H₆—C=C—CH₃, —CH₂—CH=CH—CH=CH—CH₃, —CH=CH—CH=CH—C₂H₅, —CH₂—CH=CH—C(CH₃)=CH₂, —CH₂—CH=C(CH₃)—CH=CH₂, —CH(CH₃)—CH₂—C=CH, —CH(CH₃)—CH=CH—CH=CH₂, —CH=CH—CH₂—C(CH₃)=CH₂, —CH(CH₃)—C=C—CH₃, —CH=CH—CH(CH₃)—CH=CH₂, —CH—C(CH₃)—CH₂—CH=CH₂, —C₂H₄—CH(CH₃)—C=CH, —C(CH₃)=CH—CH₂—CH=CH₂, —CH=CH—C(CH₃)₂—CH₂, —CH₂—CH(CH₃)—CH₂—C=CH, —CH=CH—C(CH₃)=CH—CH₃, —CH=C(CH₃)—CH=CH—CH₃, —CH₂—CH(CH₃)—C=CH, —CH=C(CH₃)—CH=CH—CH₃, —CH=CH—CH=CH—CH₃, —CH=C(CH₃)—C(CH₃)=CH₂, —C(CH₃)=CH—C(CH₃)=CH₂, —C(CH₃)=C(CH₃)—CH=CH₂, —CH=CH—CH=CH—

CH=CH$_2$, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —C$_3$H$_7$—C≡CH, —C$_2$H$_4$—C≡C—CH$_3$, —CH$_2$—C≡C—C$_2$H$_5$, —C≡C—C$_3$H$_7$, —CH(CH$_3$)—C≡CH, —C$_4$H$_8$—C≡CH—C$_2$H$_4$—C≡C—C$_2$H$_5$, —CH$_2$—C≡C—C$_3$H$_7$, —C≡C—C$_4$H$_9$, —C≡C—C(CH$_3$)$_3$, —CH(CH$_3$)—C$_2$C$_4$—C≡CH, —CH$_2$C≡C—CH(CH$_3$)$_2$, —C(CH$_3$)—CH$_2$—C≡C—CH$_3$, —CH(CH$_3$)—C≡C—C$_2$H$_5$, —CH$_2$—C≡C—CH(CH$_3$)$_2$, —C≡C—CH(CH$_3$)—C$_2$H$_5$, —C≡C—CH$_2$—CH(CH$_3$)$_2$, —CH(C$_2$H$_5$)—C≡C—CH$_3$, —C(CH$_3$)$_2$—C≡C—CH$_3$, —CH(C$_2$H$_5$)—CH$_2$—C≡CH, —CH$_2$—CH(C$_2$H$_5$)—C≡CH, —C(CH$_3$)$_2$—CH$_2$—C≡CH, —CH$_2$—C(CH$_3$)$_2$—C≡CH, —CH(CH$_3$)—CH(CH$_3$)—C≡CH, —CH(C$_3$H$_7$)—C≡CH, —C(CH$_3$)(C$_2$H$_5$)—C≡CH, —CH$_2$—CH(C≡CH)$_2$, —C≡C—C≡CH, —CH$_2$—C≡C—C≡CH, —C≡C—C≡C—CH$_3$, —CH(C≡CH)$_2$, —C$_2$H$_4$—C≡C—C≡CH, —CH$_2$—C≡C—CH$_2$—C≡CH, —C≡C—C$_2$H$_4$—C≡CH, —CH$_2$—C≡C—C≡C—CH$_3$, —C≡C—CH$_2$—C≡C—CH$_3$, —C≡C—C≡C—C$_2$H$_5$, —C(C≡CH)$_2$—CH$_3$, —C≡C—CH(CH$_3$)—C≡CH, —CH(CH$_3$)—C≡C—C≡CH, —CH(C≡CH)—CH$_2$—C≡CH, —CH(C≡CH)—C≡C—CH$_3$, —CH=CH-Ph, -Ph, —CH$_2$-Ph and enantiomers, stereoisomeric forms, mixtures of enantiomers, anomers, deoxy-forms, diastereomers, mixtures of diastereomers, prodrugs, tautomers, hydrates, solvates and racemates of the above mentioned compounds and pharmaceutically acceptable salts thereof.

The expression prodrug is defined as a pharmacological substance, a drug, which is administered in an inactive or significantly less active form. Once administered, the prodrug is metabolized in the body in vivo into the active compound.

The expression tautomer is defined as an organic compound that is interconvertible by a chemical reaction called tautomerization. Tautomerization can be catalyzed preferably by bases or acids or other suitable compounds.

The following subformulas (II)-(IV) of formula (I) are preferred:

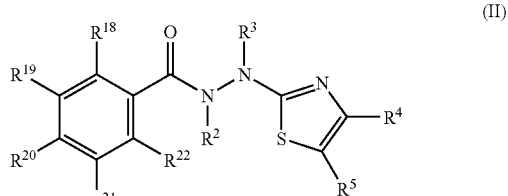
(II)

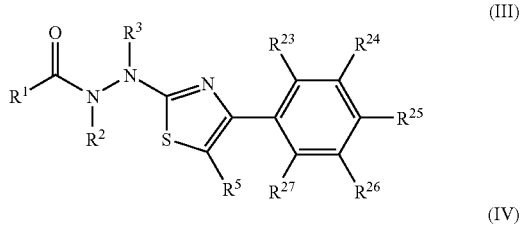
(III)

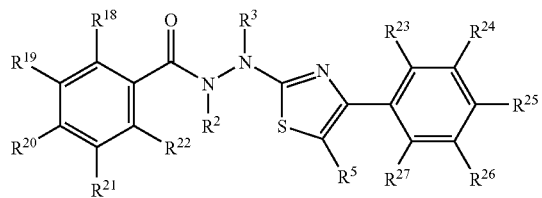
(IV)

Formulas (V)-(VII) are especially preferred:

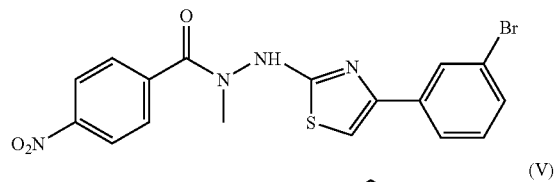
(VI)

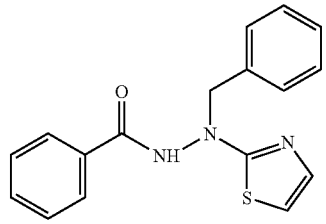
(V)

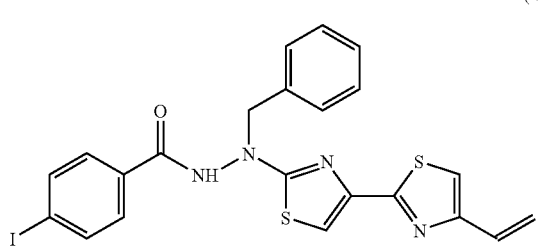
(VII)

Further preferred substitution patterns concerning moiety $R^6$ are aromatic substituents, more preferred a phenyl-ring. Preferred substituents of $R^6$ are in p-position and represent —CH$_3$, —NH$_2$, NO$_2$, —CF$_3$, —Br, —I, —F, —Cl, —CN, -Ph more preferred are halogens or nitro and most preferred is a —Cl.

Moreover it is preferred the $R^2$ and/or $R^3$ represent hydrogen or methyl.

It is also preferred that only one of the substituents $R^4$ and $R^5$ represents a group $R^7$ or $R^8$ while the other substituent of $R^4$ and $R^5$ represents hydrogen. Thus it is not preferred that both substituents $R^4$ and $R^5$ represent a group different from hydrogen. However compounds are excluded from the scope of the present embodiment wherein both substituents $R^4$ and $R^5$ represent hydrogen. Thus, it is preferred that only one of the substituents $R^4$ and $R^5$ represents hydrogen.

Moreover it is preferred that $R^1$ represents —$R^6$ or —X—$R^6$ and it is even more preferred when $R^1$ represents —$R^6$ or —NH—$R^6$ or —(CH$_2$)$_n$—$R^6$ with n=1 or 2 or 3.

Concerning $R^4$ it is preferred if $R^4$ represents —$R^7$ or —Y—$R^7$.

Concerning $R^5$ it is preferred if $R^5$ represents —$R^8$ or —Z—$R^8$. Furthermore, it is preferred when $R^5$ is —CH$_3$, —CF$_3$, —F or —Cl and especially —CH$_3$, —CF$_3$ or —F.

Not preferred are unsubstituted phenyl rigs as residue $R^1$. Thus, if $R^1$ represents a phenyl ring it is preferred that this phenyl ring has at least one substituent, preferably one substituent in para position and/or preferably one electron withdrawing substituent.

The preferred substitution pattern of $R^4$ is a heterocyclic substituent, more preferred a nitrogen-containing heterocyclic substituent and most preferred is an aromatic heterocyclic substituent containing C-, S-, N- or O-atoms or any mixture of the afore mentioned atoms having at least one nitrogen atom. This pattern is preferred if either $R^2$ or $R^3$ represents a hydrogen atom and most preferred if $R^2$ and $R^3$ are both hydrogen atoms. A preferred compound is shown in (VIII).

(VIII)

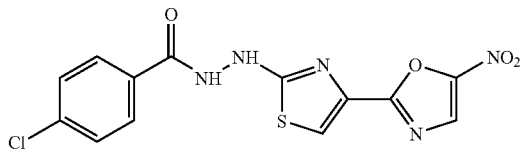

Embodiments also include pharmaceutically acceptable salts of the compounds according to the general formula (I), all stereoisomeric forms of the compounds according to the general formula (I) as well as solvates, especially hydrates or prodrugs thereof.

In case, the inventive compounds bear basic and/or acidic substituents (the compounds are definitely basic; in addition the compounds may bear acidic substituents), they may form salts with organic or inorganic acids or bases. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

Examples for suitable inorganic or organic bases are, for example, NaOH, KOH, $NH_4OH$, tetraalkylammonium hydroxide, lysine or arginine and the like. Salts may be prepared in a conventional manner using methods well known in the art, for example by treatment of a solution of the compound of the general formula (I) with a solution of an acid, selected out of the group mentioned above.

Some of the compounds may be crystallised or recrystallised from solvents such as aqueous and organic solvents. In such cases solvates may be formed. The embodiments include within its scope stoichiometric solvates including hydrates as well as compounds containing variable amounts of water that may be produced by processes such as lyophilisation.

Certain compounds of the general formula (I) may exist in the form of optical isomers if substituents with at least one asymmetric center are present, e.g. diastereoisomers and mixtures of isomers in all ratios, e.g. racemic mixtures. Embodiments disclosed herein include all such forms, in particular the pure isomeric forms. The different isomeric forms may be separated or resolved one from the other by conventional methods, or any given isomer may be obtained by conventional synthetic methods or by stereospecific or asymmetric syntheses. Where a compound according to the general formula (I) contains an alkene moiety, the alkene can be presented as a cis or trans isomer or a mixture thereof. When an isomeric form of a compound is provided substantially free of other isomers, it will preferably contain less than 5% w/w, more preferably less than 2% w/w and especially less than 1% w/w of the other isomers.

Generic Route to Thiazoihydrazides

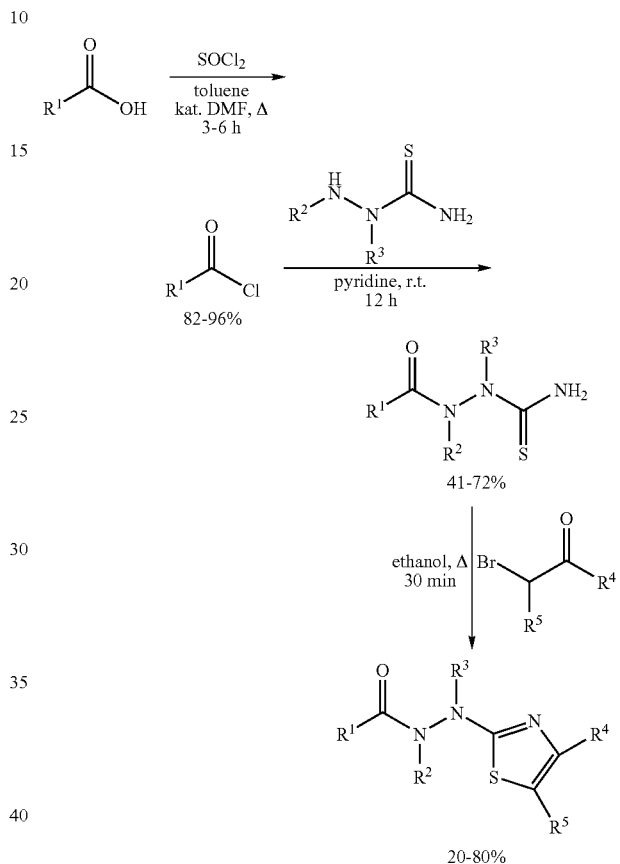

Especially preferred are the following compounds which can be synthesized according to this general route:

N'-(4-Phenylthiazol-2-yl)nicotinohydrazide (Compound 1),
N'-(4-(2-Oxo-2H-chromen-3-yl)thiazol-2-yl)nicotinohydrazide (Compound 2),
N'-(4-(4-Bromophenyl)thiazol-2-yl)-2-naphthohydrazide (Compound 3),
N'-(4-(2-Oxo-2H-chromen-3-yl)thiazol-2-yl)-2-naphthohydrazide (Compound 4),
4-Fluoro-N'-(4-(2-oxo-2H-chromen-3-yl)thiazol-2-yl)benzohydrazide (Comp. 5),
1-(4-(4-(Nitrophenyl)thiazol-2-yl)-4-phenylsemicarbazide (Compound 6),
N'-[4-(4-nitrophenyl)-1,3-thiazol-2-yl]-1,1'-biphenyl-4-carbohydrazide (Compound 7),
N'-[4-(4-Nitrophenyl)-1,3-thiazol-2-yl]-1H-benzimidazole-5-carbohydrazide (Compound 8),
N'-[4-(4-pyrrolidin-1-ylphenyl)-1,3-thiazol-2-yl]-1,1'-biphenyl-4-carbohydrazide (Compound 9),
N'-[4-(4-pyrrolidin-1-ylphenyl)-1,3-thiazol-2-yl]nicotinohydrazide (Compound 10),
N'-[4-(4-nitrophenyl)-1,3-thiazol-2-yl]nicotinohydrazide (Compound 11), N'-[4-(4-bromophenyl)-1,3-thiazol-2-yl]nicotinohydrazide (Compound 12),
N'-[4-(4-nitrophenyl)-1,3-thiazol-2-yl]-1,3-benzodioxole-5-carbohydrazide (Comp. 13),
N'-[4-(4-azidophenyl)-1,3-thiazol-2-yl]-4-fluorobenzohydrazide (Compound 14),
4-fluoro-N'-[4-(4-pyrrolidin-1-ylphenyl)-1,3-thiazol-2-yl]benzohydrazide (Comp. 15),
N'-[4-(4-pyrrolidin-1-ylphenyl)-1,3-thiazol-2-yl]-2-naphthohydrazide (Compound 16),
N'-[4-(4-nitrophenyl)-1,3-thiazol-2-yl]-2-furohydrazide (Compound 17),
4-fluoro-N'-[4-(4-nitrophenyl)-1,3-thiazol-2-yl]benzohydrazide (Compound 18),
4-chloro-N'-[5-methyl-4-(3-nitrophenyl)-1,3-thiazol-2-yl]benzohydrazide (Comp. 19),
N'-(4-(4-Nitrophenyl)thiazol-2-yl)-2-naphthohydrazide (Compound 20),
N'-[4-(4-bromophenyl)-1,3-thiazol-2-yl]isonicotinohydrazide (Compound 21),
N'-(4-phenyl-1,3-thiazol-2-yl)thiophene-2-carbohydrazide (Compound 22),
N'-[4-(3-methoxyphenyl)-1,3-thiazol-2-yl]thiophene-2-carbohydrazide (Comp. 23),
4-fluoro-N'-(4-phenyl-1,3-thiazol-2-yl)benzohydrazide (Compound 24),
2-chloro-N'-[4-(3-nitrophenyl)-1,3-thiazol-2-yl]benzohydrazide (Compound 25),
N'-[4-(1-benzofuran-2-yl)-1,3-thiazol-2-yl]-4-chlorobenzohydrazide (Compound 26),
4-chloro-N'-[4-(3-methoxyphenyl)-1,3-thiazol-2-yl]benzohydrazide (Compound 27),
N'-[4-(4-bromophenyl)-1,3-thiazol-2-yl]-2-furohydrazide (Compound 28),
4-chloro-N'-(4-thien-2-yl-1,3-thiazol-2-yl)benzohydrazide (Compound 29),
2-[4-(4-bromophenyl)-1,3-thiazol-2-yl]-N-phenylhydrazinecarboxamide (Comp. 30),
4-chloro-N'-[4-(4-fluorophenyl)-1,3-thiazol-2-yl]benzohydrazide (Compound 31),
4-fluoro-N'-(5-methyl-4-phenyl-1,3-thiazol-2-yl)benzohydrazide (Compound 32),
N'-[4-(2-oxo-2H-chromen-3-yl)-1,3-thiazol-2-yl]-1,3-benzodioxole-5-carbohydrazide (Compound 33),
4-fluoro-N'-(4-phenyl-1,3-thiazol-2-yl)benzohydrazide (Compound 34),
N'-[4-(3-methoxyphenyl)-1,3-thiazol-2-yl]isonicotinohydrazide (Compound 35),
N'-[4-(4-bromophenyl)-1,3-thiazol-2-yl]-3-phenylpropanohydrazide (Compound 36),
N'-(4-phenyl-1,3-thiazol-2-yl)-1,1'-biphenyl-4-carbohydrazide (Compound 37),
N'-[4-(4-bromophenyl)-1,3-thiazol-2-yl]-1,3-benzodioxole-5-carbohydrazide (Compound 38),
N'-[4-(4-bromophenyl)-1,3-thiazol-2-yl]-1,1'-biphenyl-4-carbohydrazide (Comp. 39),
N'-[4-(4-bromophenyl)-1,3-thiazol-2-yl]-4-fluorobenzohydrazide (Compound 40),
2-fluoro-N'-(4-phenyl-1,3-thiazol-2-yl)benzohydrazide (Compound 41),
N'-(4-phenyl-1,3-thiazol-2-yl)-2-naphthohydrazide (Compound 42),
N'-[4-(4-bromophenyl)-1,3-thiazol-2-yl]-1H-benzimidazole-5-carbohydrazide (Compound 43),
N'-8H-indeno[1,2-d][1,3]thiazol-2-yl-1,3-benzodioxole-5-carbohydrazide (Comp. 44),
N'-(4-phenyl-1,3-thiazol-2-yl)-1,3-benzodioxole-5-carbohydrazide (Compound 45),
4-chloro-M-(4-phenyl-1,3-thiazol-2-yl)benzohydrazide (Compound 46),
N'-[4-(2-oxo-2H-chromen-3-yl)-1,3-thiazol-2-yl]-1,1'-biphenyl-4-carbohydrazide (Compound 47),
N'-(4-tert-butyl-1,3-thiazol-2-yl)-4-chlorobenzohydrazide (Compound 48),
N'-[4-(4-methoxyphenyl)-1,3-thiazol-2-yl]piperidine-1-carbohydrazide (Compound 49),
N'-[4-(2-naphthyl)-1,3-thiazol-2-yl]-4-(trifluoromethyl)benzohydrazide (Compound 50),
N'-[4-(4-hydroxy-3,5-dimethoxyphenyl)-1,3-thiazol-2-yl]-4-(trifluoromethyl)benzohydrazide (Compound 51),
N'-8H-indeno[1,2-d][1,3]thiazol-2-yl-1H-indole-2-carbohydrazide (Compound 52),
N'-[4-(4-hydroxy-3,5-dimethoxyphenyl)-1,3-thiazol-2-yl]-1H-indole-2-carbohydrazide (Compound 53),
N'-[4-(2-adamantyl)-1,3-thiazol-2-yl]-1H-indole-2-carbohydrazide (Compound 54),
N'-[4-(4-chlorophenyl)-1,3-thiazol-2-yl]-1H-indole-2-carbohydrazide (Compound 55),
N'-[4-(4-isobutyloxyphenyl)-1,3-thiazol-2-yl]-1H-indole-2-carbohydrazide (Comp. 56),
N'-[4-(4-cyanophenyl)-1,3-thiazol-2-yl]-1H-indole-2-carbohydrazide (Compound 57),
N'-[4-(1,1'-biphenyl-4-yl)-1,3-thiazol-2-yl]-1H-indole-2-carbohydrazide (Comp. 58),
N'-[4-(2-naphthyl)-1,3-thiazol-2-yl]-1H-indole-2-carbohydrazide (Compound 59),
N'-[4-(2-bromophenyl)-1,3-thiazol-2-yl]-1H-indole-2-carbohydrazide (Compound 60),
N'-[5-methyl-4-(4-nitrophenyl)-1,3-thiazol-2-yl]-1,1'-biphenyl-4-carbohydrazide (Compound 61),
N'-[5-(4-bromophenyl)-4-methyl-1,3-thiazol-2-yl]-1H-benzimidazole-5-carbohydrazide (Compound 62),
N'-[5-(4-bromophenyl)-4-methyl-1,3-thiazol-2-yl]-4-fluorobenzohydrazide (Comp. 63),
N'-[5-(4-bromophenyl)-4-methyl-1,3-thiazol-2-yl]-1,1'-biphenyl-4-carbohydrazide (Compound 64),
N'-[4-(2-adamantyl)-1,3-thiazol-2-yl]-4-mathoxybenzohydrazide (Compound 65),
N'-8H-indeno[1,2-d][1,3]thiazol-2-yl-4-(trifluoromethyl)benzohydrazide (Comp. 66),
N'-[4-(4-cyanophenyl)-1,3-thiazol-2-yl]-3-fluorobenzohydrazide (Compound 67),
N'-[4-(4-chlorophenyl)-1,3-thiazol-2-yl]cyclohexanecarbohydrazide (Compound 68),
N'-[4-(4-methoxyphenyl)-1,3-thiazol-2-yl]benzohydrazide (Compound 69),
2-fluoro-N'-[4-(4-methoxyphenyl)-1,3-thiazol-2-yl]benzohydrazide (Compound 70),
N'-[4-(4-chlorophenyl)-1,3-thiazol-2-yl]benzohydrazide (Compound 71),
N'-[4-(4-chlorophenyl)-1,3-thiazol-2-yl]-2-fluorobenzohydrazide (Compound 72),
2-fluoro-N'-[4-(3-nitrophenyl)-1,3-thiazol-2-yl]benzohydrazide (Compound 73),
N'-[4-(1,1'-biphenyl-4-yl)-1,3-thiazol-2-yl]-2-fluorobenzohydrazide (Compound 74),
6-fluoro-N'-[4-(4-pyrrolidin-1-ylphenyl)-1,3-thiazol-2-yl]nicotinohydrazide (Com. 75),
N-methyl-N'-[4-(4-nitrophenyl)-1,3-thiazol-2-yl]-1,1'-biphenyl-4-carbohydrazide (Compound 76),
N,N'-dimethyl-N'-[4-(4-nitrophenyl)-1,3-thiazol-2-yl]-1,1'-biphenyl-4-carbohydrazide (Compound 77).

Excluded from the scope of the present compounds claims but not excluded from the use claims are the following compounds:

nicotinic acid N'-(4-phenyl-thiazol-2-yl)-hydrazide;
4-nitro-benzoic acid N'-phenyl-N'-(4-phenyl-thiazol-2-yl)-hydrazide;
4-(p-chlorophenyl)-2-isonicotinylhydrazinothiazole;
benzoic acid N'-(4-benzothiazol-2-yl-thiazol-2-yl)-hydrazide;
benzoic acid N'-(4-naphthalen-2-yl-thiazol-2-yl)-hydrazide;
2-(N'-benzoylhydrazino)-4-(4-chlorophenyl)thiazole;
isonicotinic acid N'-[4-(4-methoxy-phenyl)-thiazol-2-yl]-hydrazide;
2-chloro-benzoic acid N'-[4-(4-bromo-phenyl)-thiazol-2-yl]-hydrazide;
isonicotinic acid N'-(4-phenyl-thiazol-2-yl)-hydrazyde;
benzo[1,3]dioxole-5-carboxylic acid N'-(4-phenyl-thiazol-2-yl)-hydrazide;
benzo[1,3]dioxole-5-carboxylic acid N'-(4-methyl-thiazol-2-yl)-hydrazide;
benzo[1,3]dioxole-5-carboxylic acid N'-[4-(4-methoxy-phenyl)-thiazol-2-yl]-hydrazide;
3,4,5-trimethoxy-benzoic acid N'-(4-phenyl-thiazol-2-yl)-hydrazide;

as well as compounds wherein
R$^4$ is

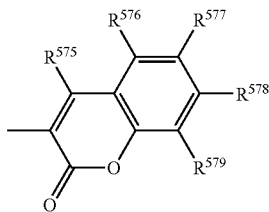

and R$^1$ is phenyl or para-nitrophenyl.

Another embodiment relates to the use of the inventive thiazolhydrazide derivatives as drugs, i.e. as pharmaceutically active agents applicable in medicine.

Surprisingly it was found that the above-mentioned thiazolhydrazide derivatives as well as the pharmaceutical compositions including said thiazolhydrazide derivatives are useful for treatment of neurodegenerative diseases, disorders and conditions.

Thus, the thiazolhydrazide compounds can be used for prophylaxis and treatment of neurodegenerative diseases, disorders and conditions, or for the preparation of a pharmaceutical formulation for prophylaxis and treatment of neurodegenerative diseases, disorders and conditions.

Among the hundreds of different neurodegenerative disorders, the attention has been given only to a handful, including Alzheimer Disease, Parkinson Disease, Huntington Disease, and amyotrophic lateral sclerosis.

It is worth to mention that the same neurodegenerative process can affect different areas of the brain, making a given disease appear very different from a symptomatic standpoint.

Neurodegenerative disorders of the central nervous system (CNS) can be grouped into diseases of the cerebral cortex (Alzheimer Disease), the basal ganglia (Parkinson Disease), the brain-stem and cerebellum, or the spinal cord (amyotrophic lateral sclerosis).

Examples for neurodegeneration and neurodegenerative diseases and disorders which can be treated and/or prevented by the inventive compounds are Alzheimer Disease, Parkinson Disease, Huntington Disease, amyotrophic lateral sclerosis, AIDS-related dementia, retinitis pigmentosa, spinal muscular atrophy and cerebrellar degeneration, fragile X-associated tremor/ataxia syndrome (FXTAS), progressive supranuclear palsy (PSP), and striatonigral degeneration (SND), which is included with olivopontocerebellear degeneration (OPCD), and Shy Drager syndrome (SDS) in a syndrome known as multiple system atrophy (MSA).

Therefore, another embodiment is directed to pharmaceutical compositions including at least one compound described herein as active ingredient, together with at least one pharmaceutically acceptable carrier, excipient and/or diluents. The pharmaceutical compositions may be prepared in a conventional solid or liquid carrier or diluent and a conventional pharmaceutically-made adjuvant at suitable dosage level in a known way. The preferred preparations are adapted for oral application. These administration forms include, for example, pills, tablets, film tablets, coated tablets, capsules, powders and deposits.

Furthermore, embodiments include pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain at least one compound described herein and/or a pharmaceutical acceptable salt thereof as active ingredient.

The pharmaceutical compositions include at least one compound described herein, and/or a pharmaceutical acceptable salt thereof as active ingredient will typically be administered together with suitable carrier materials selected with respect to the intended form of administration, i.e. for oral administration in the form of tablets, capsules (either solid filled, semi-solid filled or liquid filled), powders for constitution, extrudates, deposits, gels, elixirs, dispersable granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like. Moreover, suitable binders, lubricants, disintegrating agents and coloring agents may also be incorporated into the tablet or capsule. Powders and tablets may contain about 5 to about 95 weight % of the benzothiophene-1,1-dioxide derived compound and/or the respective pharmaceutically active salt as active ingredient.

Suitable binders include starch, gelatin, natural sugars, corn sweeteners, natural and synthetic gums such as acacia, sodium alginate, carboxymethylcellulose, polyethylene glycol and waxes. Among suitable lubricants there may be mentioned boric acid, sodium benzoate, sodium acetate, sodium chloride, and the like. Suitable disintegrants include starch, methylcellulose, guar gum, and the like. Sweetening and flavoring agents as well as preservatives may also be included, where appropriate. The disintegrants, diluents, lubricants, binders etc. are discussed in more detail below.

Moreover, the pharmaceutical compositions may be formulated in sustained release form to provide the rate controlled release of any one or more of the components or active ingredients to optimise the therapeutic effect(s), e.g. antihistaminic activity and the like. Suitable dosage forms for sustained release include tablets having layers of varying disintegration rates or controlled release polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration. Aerosol preparations suitable for inhalation may include solutions and solids in powder form, which may be present in combination with a pharmaceutically acceptable carrier such as an inert, compressed gas, e.g. nitrogen. For preparing suppositories, a low melting fat or wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations which are intended to be converted, shortly before use, to liquid form preparations for either oral or parenteral administration. Such liquid forms include solutions, suspensions, and emulsions.

The compounds described herein may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methyl cellulose, polyvinyl alcohols, or denatured gelatins or starch for holding or containing compositions including the active ingredient(s). Capsules with hard shells are typically made of blended of relatively high gel strength gelatins from bones or pork skin. The capsule itself may contain small amounts of dyes, opaquing agents, plasticisers and/or preservatives. Under tablet a compressed or moulded solid dosage form is understood which includes the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilised in a hydrophilic semi-solid matrix. Powders for constitution refers to powder blends containing the active ingredients and suitable diluents which can be suspended e.g. in water or in juice.

Suitable diluents are substances that usually make up the major portion of the composition or dosage form. Suitable diluents include sugars such as lactose, sucrose, mannitol, and sorbitol, starches derived from wheat, corn rice, and potato, and celluloses such as microcrystalline cellulose. The amount of diluent in the composition can range from about 5 to about 95% by weight of the total composition, preferably from about 25 to about 75 weight %, and more preferably from about 30 to about 60 weight %.

The term disintegrants refers to materials added to the composition to support break apart (disintegrate) and release the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscaramellose, alginates such as alginic acid and sodium alginate, clays such as bentonites, and effervescent mixtures. The amount of disintegrant in the composition may range from about 2 to about 20 weight % of the composition, more preferably from about 5 to about 10 weight %.

Binders are substances which bind or "glue" together powder particles and make them cohesive by forming granules, thus serving as the "adhesive" in the formulation. Binders add cohesive strength already available in the diluent or bulking agent. Suitable binders include sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20 weight % of the composition, preferably from about 3 to about 10 weight %, and more preferably from about 3 to about 6 weight %.

Lubricants refer to a class of substances which are added to the dosage form to enable the tablet granules etc. after being compressed to release from the mould or die by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules. The amount of lubricant in the composition may range from about 0.2 to about 5 weight % of the composition, preferably from about 0.5 to about 2 weight %, and more preferably from about 0.3 to about 1.5 weight % of the composition.

Glidents are materials that prevent caking of the components of the pharmaceutical composition and improve the flow characteristics of granulate so that flow is smooth and uniform. Suitable glidents include silicon dioxide and talc. The amount of glident in the composition may range from about 0.1 to about 5 weight % of the final composition, preferably from about 0.5 to about 2 weight %.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5 weight % of the composition, preferably from about 0.1 to about 1 weight %.

Said pharmaceutical compositions may further include at least one active thiazolhydrazide of the general formula (I) or subformulas (II)-(IV).

The pharmaceutical compositions may further include at least one drug selected from the group comprising meclofenoxate, nicergoline, piracetame, pyritinole, tacrine, donezepiel, galantamine, rivastigmine, memantine, IMPase-inhibitors and extracts from Gingko biloba.

Figure 1:
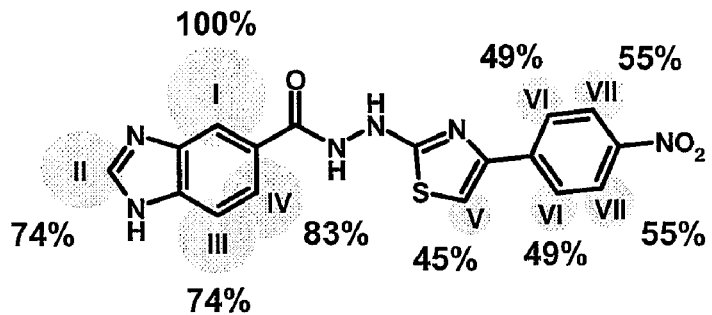
FIG. 1: Binding epitope of compound BSc3094 (compound 8) with tau construct K18 derived from STD NMR. Effects larger than 50% form the binding epitope.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

Examples

General Procedure for the Synthesis of Thiazolhydrazides

Carbonic acid (20 mmol), thionylchloride (40 mmol) and a catalytical amount of DMF are mixed with toluene (20 mL) and heated to reflux for 3-6 h. The mixture is cooled to r.t. and concentrated in vacuo. The crude product is dried at 0.1 mbar, when appropriate. The acyl chlorides are added without further purification to thiosemicarbazide (4 mmol) in dry pyridine (4 mL) at 0° C. The mixture is stirred for further 12 h at r.t. Excess pyridine is removed in vacuo. The crude mixture was crystallised from ethanol to remove pyridinium-hydrochloride.

The acylated thiosemicarbazide (0.5 mmol) was dissolved in 3 mL of ethanol. Bromoacetophenone (0.5 mmol) was added, and the mixture was refluxed for 30 min. The product precipitated on cooling to r.t. The salt was suspended in dichloromethane and neutralized by NaHCO₃-sol. (3×25 mL) and washed with brine (1×25 mL). The dichloromethane extract was dried over MgSO₄ and concentrated in vacuo. The crude product was recrystallised (ethylacetate, ethanol) or purified by chromatography (silica gel, ethylacetate/hexane) to provide the final compound in >95% purity.

Example 1

N'-(4-Phenylthiazol-2-yl)nicotinohydrazide (Compound 1)

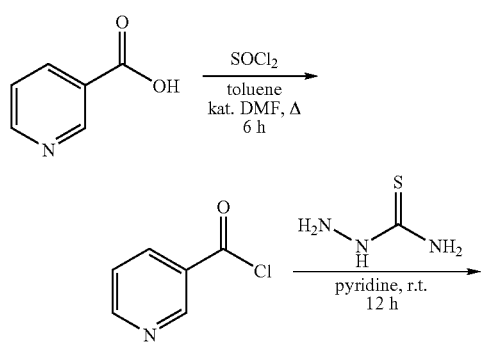

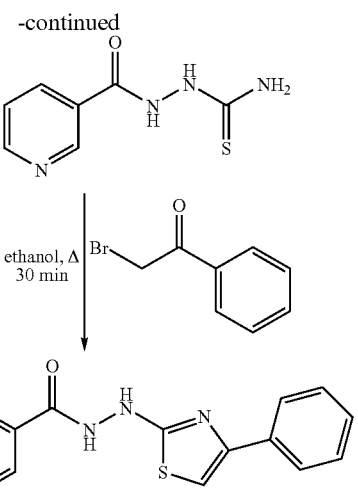

$^1$H-NMR (300 MHz, DMSO-$d_6$): δ=11.10 (s, 1H, 5-NH); 9.78 (s, 1H, 6-NH); 9.10 (s, 1 arom. H, 1-CH); 8.80 (d, 1 arom. H, 2-CH, J=3.7 Hz); 8.27 (d, 1 arom. H, 4-CH, J=8.0 Hz); 7.84 (d, 2 arom. H, 8-CH, J=7.4 Hz); 7.60 (dd, 1 arom. H, 3-CH, J=4.9. 7.8 Hz); 7.40 (t, 2 arom. H, 9-CH, J=7.5 Hz); 7.32-7.27 (m, 2H, arom. H, 10-CH, thiazol) ppm.

Example 2

N'-(4-(2-Oxo-2H-chromen-3-yl)thiazol-2-yl)nicotinohydrazide (Compound 2)

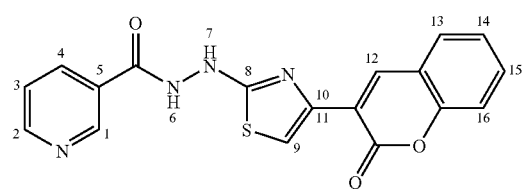 [SMILES: O=C(NNc1nc(-c2cc3ccccc3oc2=O)cs1)c1cccnc1]

$^1$H-NMR (300 MHz, DMSO-$d_6$): δ=11.16 (s, 1H, 6-NH); 9.85 (s, 1H, 7-NH); 9.08 (s, 1 arom. H, 1-CH); 8.80 (d, 1 arom. H, 2-CH, J=3.6 Hz); 8.57 (s, 1 arom. H, 12-CH); 8.27 (d, 1 arom. H, 4-CH, J=7.9 Hz); 7.88 (d, 1 arom. H, 3-CH, J=7.2 Hz); 7.73 (s, 1H, 9-CH, Thiazol); 7.65-7.59 (m, 2 arom. H, 13-CH, 15-CH); 7.46-7.39 (m, 2 arom. H, 14-CH, 16-CH) ppm.

Example 3

N'-(4-(4-Bromophenyl)thiazol-2-yl)-2-naphthohydrazide (Compound 3)

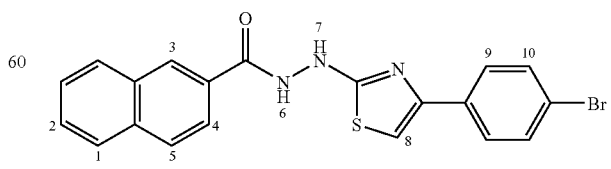

$^1$H-NMR (300 MHz, DMSO-$d_6$): δ=11.05 (s, 1H, 6-NH); 9.78 (s, 1H, 7-NH); 8.55 (s, 1 arom. H, 3-CH); 8.10-7.96 (m, 4 arom. H, 1-CH, 4-CH, 5-CH); 7.80 (d, 2 arom. H, 10-CH, J=8.5 Hz); 7.67-7.63 (m, 2 arom. H, 2-CH); 7.59 (d, 2 arom. H, 9-CH, J=8.5 Hz); 7.36 (s, 1H, 8-CH Thiazol-H) ppm.

Example 4

N'-(4-(2-Oxo-2H-chromen-3-yl)thiazol-2-yl)-2-naphthohydrazide (Compound 4)

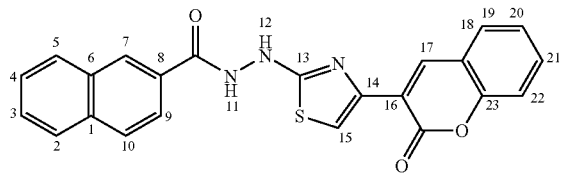

$^{1}$H-NMR (300 MHz, DMSO-d$_{6}$): δ=11.12 (s, 1H, 11-NH); 9.84 (s, 1H, 10-NH); 8.59 (s, 1 arom. H, 17-CH); 8.57 (s, 1 arom. H, 7-CH); 8.10-8.00 (m, 4 arom. H, 9-CH, 10-CH, 2-CH); 7.87 (d, 1 arom. H, 19-CH, J=7.1 Hz); 7.74 (s, 1 arom. H, 15-CH, Thiazol); 7.66-7.60 (m, 3 arom. H, 3-CH, 4-CH, 21-CH); 7.44 (d, 1 arom. H, 22-CH, J=8.2 Hz); 7.38 (t, 1 arom. H, 20-CH, J=7.3 Hz) ppm.

$^{13}$C-NMR (75 MHz, DMSO-d$_{6}$): δ=172.9 (13-C, Thiazol); 167.4 (CONR); 159.4 (COOR); 153.0 (14-C, Thiazol); 144.8 (23-C); 139.1 (17-CH); 135.2 (6-CH); 132.7 (8-C); 132.3 (5-CH); 130.3 (1-C); 129.7 (7-CH); 129.5 (3-CH); 129.0 (10-CH); 128.8 (2-CH); 128.4 (4-CH); 127.7 (19-C); 125.4 (20-C); 124.5 (9-CH); 121.1 (16-C); 119.9 (18-C); 116.5 (22-CH); 110.7 (15-CH, Thiazol) ppm.

Example 5

4-Fluoro-N'-(4-(2-oxo-2H-chromen-3-yl)thiazol-2-yl)benzohydrazide (Comp. 5)

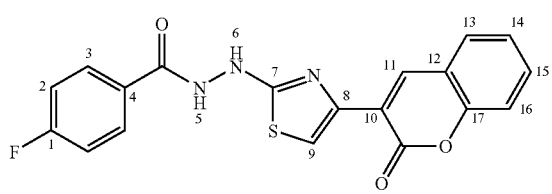 [SMILES: O=C(NNc1nc(-c2cc3ccccc3oc2=O)cs1)c1ccc(F)cc1]

$^{1}$H-NMR (300 MHz, DMSO-d$_{6}$): δ=10.99 (s, 1H, 5-NH); 9.78 (s, 1H, 6-NH); 8.96 (s, 1 arom. H, 11-CH); 8.03-7.98 (m, 2 arom. H, 3-CH); 7.87 (d, 1 arom. H, 13-CH, J=7.5 Hz); 7.70 (s, 1 arom. H, 9-CH, Thiazol-H); 7.60 (dd, 1 arom. H, 15-CH, J=7.8, 15.2 Hz); 7.45-7.36 (m, 4 arom. H, 2-CH, 14-CH, 16-CH) ppm.

$^{13}$C-NMR (75 MHz, DMSO-d$_{6}$): δ=172.1 (7-C, Thiazol); 165.8 (C—F); 158.7 (CONR); 152.2 (COOR); 149.5 (17-C); 146.2 (11-CH); 144.0 (8-C, Thiazol); 135.8 (4-C); 131.1 (10-C); 130.1 (3-CH); 128.9 (15-CH); 127.7 (13-CH); 125.5 (14-CH); 124.6 (16-CH); 120.4 (12-C); 115.6 (2-CH); 110.0 (9-CH, Thiazol) ppm.

Example 6

1-(4-(4-(Nitrophenyl)thiazol-2-yl)-4-phenylsemicarbazide (Compound 6)

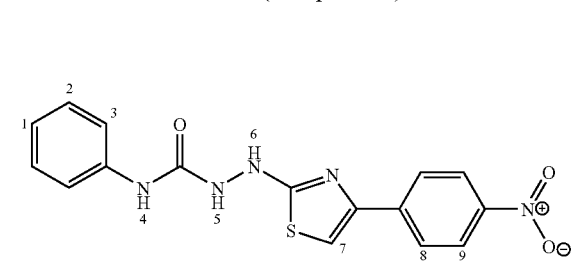

$^{1}$H-NMR (300 MHz, DMSO-d$_{6}$): δ=9.58 (s, 1H, 5-NH); 9.03 (s, 1H, 4-NH); 8.78 (s, 1H, 6-NH); 8.27 (d, 2 arom. H, 9-CH, J=8.7 Hz); 8.1 (d, 2 arom. H, 8-CH, J=8.7 Hz); 7.67 (s, 1H, 7-CH, Thiazol-H); 7.53 (d, 2 arom. H, 3-CH, J=7.9 Hz); 7.25 (t, 2 arom. H, 2-CH, J=7.8 Hz); 6.96 (t, 1 arom. H, 1-CH, J=7.3 Hz) ppm.

Example 7

N'-[4-(4-Nitrophenyl)-1,3-thiazol-2-yl]-1H-benzimidazole-5-carbohydrazide (Compound 8)

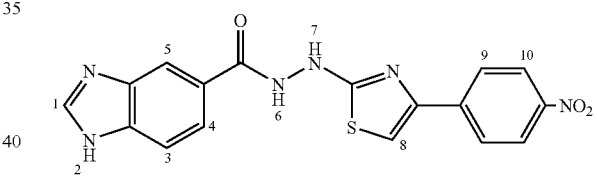

The crude product obtained from the generic procedure was recrystallized from ethyl acetate to provide 88 mg (31%) of N'-(4-(4-(Nitrophenyl)thiazol-2-yl)-1H-benz[d]imidazol-5-carbhydrazid as pale yellow green solid.

$^{1}$H-NMR (300 MHz, DMSO-d$_{6}$): δ=12.74 (s, 1H, 2-NH), 10.89 (s, 1H, 6-NH), 9.79 (s, 1H, 7-NH), 8.38-8.11 (m, 6H, 1-H, 3-H, 4-H, 5-H, 10-H), 7.80-7.64 (m, 3H, 8-H, 9-H) ppm.

Example 8

N'-8H-indeno[1,2-d][1,3]thiazol-2-yl-1,3-benzodioxole-5-carbohydrazide (Compound 44)

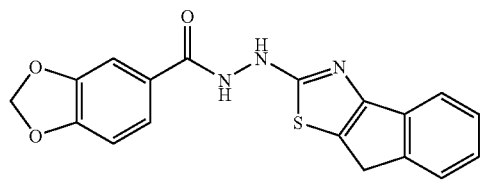 [SMILES: O=C(NNc1nc2c(s1)Cc1ccccc1-2)c1ccc2c(c1)OCO2]

The crude product obtained from the generic procedure was recrystallized from ethyl acetate to provide 33% of compound 44.

Example 9

Generation of Biological Data

Thioflavine S (ThS) Assay for aggregation of tau: 10 µM of the tau construct K19 were incubated with compounds in a concentration range from 1 nM up to 200 µM in the presence of 2.5 µM heparin in 50 mM NH$_4$Ac buffer over night at 37° C. After addition of 20 µM ThS the signal was measured at 521 nm (emission) at an excitation wavelength of 440 nm. The results of this assay are presented in the IC50 column and DC50 column of Table 1 below.

Selection of an N2a, Tet-On, G418-resistant cell line: N2a cells were cotransfected with both the pUHD172-1 plasmid (encoding the rtTA, obtained from H. Bujard, Heidelberg) and pEU-1 plasmid (encoding G418 resistance, a derivative of pRc/CMV, Invitrogen) (ratio 20:1; 1 µg/well of 6-well plates) using the DOTAP transfection reagent (Roche, Basel, CH). The cells were cultured in Eagle's Minimum Essential Medium (MEM) supplemented with 10% defined fetal bovine serum and subjected to G418 (600 µg/ml) and selection. The cells were fed with fresh media every 4 days for 3-4 weeks when single colonies appeared. Clones were tested for the induction level by transient transfection of pUHG 16-3 plasmid and the induction of β-galactosidase was measured. The pBI-5 plasmid was also transiently transfected into these cells, the luciferase assay showed 230-fold induction.

Generation of inducible Tet-On cell lines: The DNA fragments encoding the appropriate tau constructs (K18WT, K18ΔK280, K18/ΔK280/PP) were inserted into the bidirectional vector pBI-5 between ClaI and SalI restriction sites (pBI-5 is an unpublished derivative of pBI-2, Baron et al., 1995). The pBI-5/K18-derived plasmids with pX343 (plasmid encoding the hygromycin resistance) were used for cotransfection of N2a/Tet-On, G418-resistant cells with the aid of DOTAP (20:1 plasmid ratio; 1 µg/well of 6-well plates). The cells were seeded at 4×10$^5$ cells per well. On the following day cells were transferred to 100-mm dishes and selected with 100 µg/ml of hygromycin and 600 µg/ml of G418. Clonal cell lines were screened for the inducible expression of K18 derivatives by measuring luciferase activity with the luciferase assay and immunofluorescence for tau protein with the polyclonal pan-tau antibody K9JA.

Induction of K18-derivatives in Tet-On N2a cells: The inducible N2a/K18-derivatives cells were cultured in MEM medium supplemented with 10% fetal calf serum, 2 mM glutamine and 0.1% nonessential amino acids. The expression of K18 constructs was induced by adding 1 µg doxycyclin (Dox) per 1 ml medium. The induction was continued for 7-11 days, the medium was changed 3 times (always complemented with doxycyclin). For tau solubility assays the cells were collected by pelleting during centrifugation at 1000×g for 5 min. The levels and solubility of tau K18/ΔK280 were determined following Greenberg and Davies (1990). The cells were homogenized (DIAX900, Heidolph, Schwabach, Germany) in 10 vol (w/v) of buffer consisting of 10 mM Tris-HCl (pH 7.4), 0.8 M NaCl, 1 mM EGTA, and 10% sucrose. The homogenate was spun for 20 min at 20000×g, and the supernatant was retained. The pellet was re-homogenized in 5 vol of homogenization buffer and re-centrifuged. Both supernatants were combined, brought to 1% N-laurylsarkosinate (w/v) and incubated for 1 hr at room temperature while shaking, followed by centrifugation at 100 000×g for 1 hr. The sarkosyl-insoluble pellets were resuspended in 50 mM Tris-HCl (pH 7.4), 0.5 ml per 1 g of starting material. The supernatant and sarkosyl-insoluble pellet samples were analyzed by Western blotting. The amount of material loaded for supernatant and sarkosyl-insoluble pellet represented about 0.5% and 15% of the total material present in the supernatant and pellet respectively (the ratio between supernatant and sarkosyl insoluble pellet was always 1:30). For quantification of tau levels in each fraction, the Western blots were probed with pan-tau antibody K9JA and analyzed by densitometry (LAS 3000 and AIDA software, Raytest, Straubenhardt, Germany).

Quantitation of tau aggregation in cells by Thioflavin S (ThS) staining: Tet-On inducible undifferentiated N2a cells were treated with 1 µg/ml doxycyclin for 5, 7 or 9 days in a culture dish. After that the cells were trypsinized and transferred to coverslips and incubated overnight. The cells on the coverslips were fixed with 4% paraformaldehyde in PBS for 15 min, then permeabilized with 80% MeOH for 6 min at −20° C., and incubated with 0.1% Thioflavin S for 5 min and washed three times in ethanol (50%). The samples were incubated with antibody K9JA in 5% goat serum (PBS). The secondary anti rabbit antibody labeled with Cy5 was also diluted with 5% goat serum in PBS and incubated for 45 min. The cells were washed twice with PBS, once with water and mounted. Cells containing distinct ThS signals indicating the presence of insoluble aggregated material with β-pleated sheets were scored in many independent fields containing a total of 500 cells.

Neurotoxicity assay: Neurotoxicity was assessed using an LDH (lactate dehydrogenase) assay kit (Roche, Mannheim, Germany) according to the manufacturer's specifications. In the viability assay the aggregation inhibitor compound was added at a final concentration of 10 µM to uninduced N2A cells. The activity of LDH was measured spectrophotometrically at 492 nm. Cell death was calculated as percent of LDH released into medium, compared to total LDH obtained after total cell lysis. The results of this assay are presented in the LDH column of Table 1 below.

Tau aggregation and inhibition assay in cells: The N2a/K18ΔK280 cells were grown in Nunc flasks in MEM medium supplemented with G418 (300 µg/ml) and Hygromycin (100 µg/ml). The protein expression in the control sample was induced by addition of 1 µg/ml doxycyclin (final concentration) and cells were incubated for 5 days. In the inhibition assay the aggregation inhibitor compound was added together with doxycyclin at a final concentration of 10 µM. After 5 days of protein expression the cells were transferred to glass coverslips coated with polylysine, fixed with 3.7% paraformaldehyde in PBS, and briefly permeabilized with 80% MeOH. Next the cells were incubated with 0.01% Thioflavin-S, followed by incubation with rabbit antibody K9JA and secondary anti rabbit antibody labeled with Cy5. For assaying the dissolution of preformed tau aggregates the inducible N2a cells were incubated with 1 µg/ml doxycyclin for 5 days. After that the medium was exchanged for a new one containing 1 µg/ml doxycyclin and 10 µM of the inhibitor compound and the incubation was continued for two more days. Transfer of cells onto cover slips and staining with ThS and Tau antibody was performed as above. Finally the cells showing ThS staining were scored in independent fields containing at least 500 cells. The results of this assay are presented in the Inhibition in cells column of Table 1 below.

STD-NMR: All STD NMR experiments were made in 3 mm Match® tubes in a 700 MHz spectrometer with cryogenic probe head at 295 K. The quantity of protein was kept small by the small diameter of the sample tubes. The spectra were measured with a spectral width of 11.0208 ppm and 32k data points with application of the WATERGATE water suppression (w5-sequence). The suppression of the protein resonances was reached by a spin lock pulse with a length of 15 ms and a attenuation of 11 dB. We used a pulse program in which the presaturation was accomplished alternating after each scan for the on and off resonance experiment at the selected frequencies. Thus artefacts are prevented during the difference formation due to in homogeneities. As point of irradiation for the on resonance experiments we selected 540 Hz (0.77 ppm). As point of irradiating for the off resonance experiments 40,000 Hz (57.1 ppm) was selected. The saturation duration in all experiments was 4 seconds, the attenuation of the saturation power 45 dB. 2044 scans were collected per experiment. After phase correction the FID was multiplied by an exponential function to improve the signal to noise ratio, which caused a line broadening of 1 Hz.

For the determination of the binding epitope a sample with 33.33 µM BSc3094, µM soluble K18 and 80 µM DTT-d$_6$ in 200 µL PBS/D$_2$O was used. Subsequently, STD spectrum and reference spectrum were compared with one another and the magnitude of the STD effects and the binding epitope were determined. FIG. 1 demonstrates the binding epitope of compound BSc3094 with tau construct K18 derived from STD NMR. Effects larger than 50% form the binding epitope.

Figure 2:
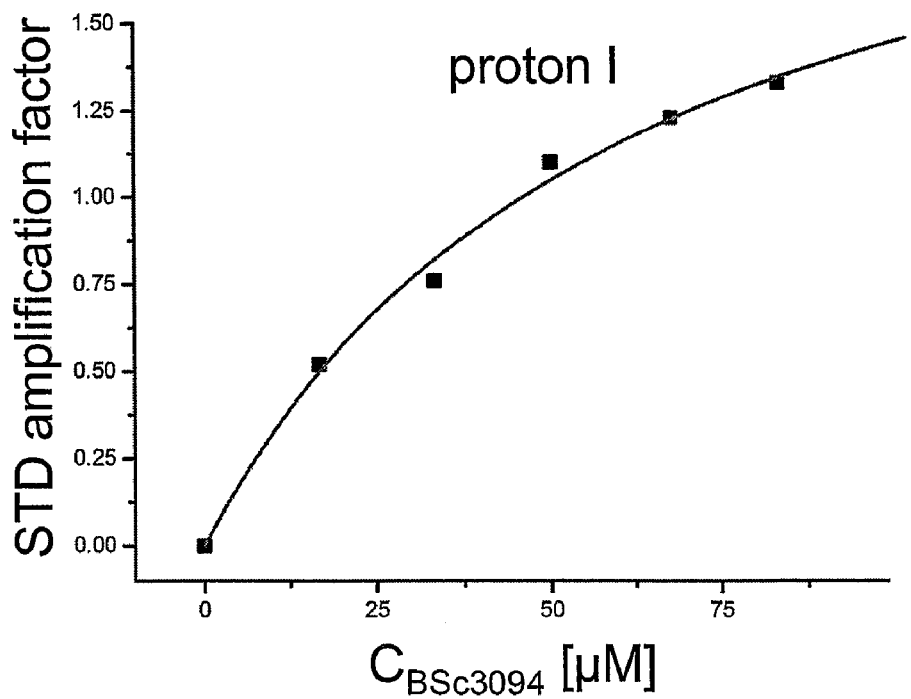
FIG. 2: Determination of dissociation constant of K18-BSc3094 (compound 8) complex by STD-NMR using the titration data for proton I. Regression analysis of the data yields a $K_D = 62 \pm 12$ μM.

For the determination of the dissociation constant a sample with 10 µM soluble K18 and 80 µM DTT-d$_6$ in 200 µL PBS/D$_2$O was prepared. Then the concentration of BSc3094 was varied to 16.7, 33.3, 50.0, 67.7, 83.3, 100.0 and 200.0 µM. This corresponds to a change of the excess of BSc3094 to the tau construct of 1.67-fold to 20-fold. Evaluation of the data until 83.3 µM resulted in the dissociation constants. FIG. 2 demonstrates the determination of dissociation constant of K18-BSc3094 complex by STD-NMR using the titration data for proton I. Regression analysis of the data yields a $K_D = 62 \pm 12$ µM.

Surface plasmon resonance: Surface plasmon resonance experiments were accomplished at a Biacore T100 instrument at a temperature of 298 K using CM5-Chips. As buffer system sterile PBS buffer with 1% DMSO was used. 325 fmol of soluble tau construct K18 was immobilized. We selected for the regeneration a 20 second injection with 50 mM of hydrochloric acid followed by 60 seconds as a stabilization period. A flow rate of 30 µL/min was selected. As time of contact the maximally possible time of 700 seconds and as dissociation and a stabilization time in each case 300 seconds were selected. The evaluation of the kinetic data was accomplished by use of the Biacore T100 evaluation software.

TABLE 1

Chemical compounds together with the IC$_{50}$, DC$_{50}$ and cell inhibition data.

[General structure: R$^1$–C(=O)–N(R$^2$)–N(R$^3$)–[thiazole with R$^4$, R$^5$ substituents]]

| | R1 | R2 | R3 | R4 |
|---|---|---|---|---|
| Comp. 7 BSc2998 | 4-biphenyl (X at para) | H | H | 4-nitrophenyl (X) |
| Comp. 8 BSc3094 | 5-benzimidazolyl (X) | H | H | 4-nitrophenyl (X) |
| Comp. 9 BSc3000 | 4-biphenyl (X at para) | H | H | 4-(pyrrolidin-1-yl)phenyl (X) |
| Comp. 10 BSc3551 | 3-pyridyl (X) | H | H | 4-(pyrrolidin-1-yl)phenyl (X) |

TABLE 1-continued
| | | | | |
|---|---|---|---|---|
| Comp. 11 BSc2994 | 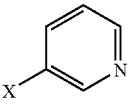 | H | H | 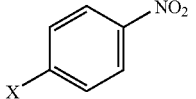 |
| Comp. 12 BSc2997 | 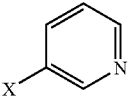 | H | H | 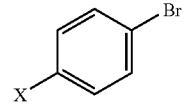 |
| Comp. 13 BSc3016 | 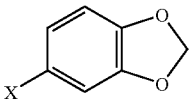 | H | H | 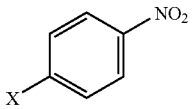 |
| Comp. 14 BSc3012 | 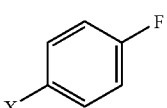 | H | H | 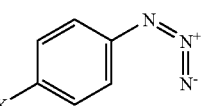 |
| Comp. 15 BSc2991 | 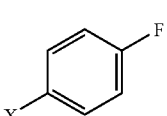 | H | H | 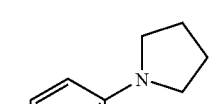 |
| Comp. 16 BSc3055 | 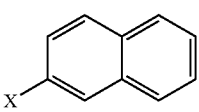 | H | H | 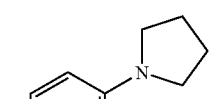 |
| Comp. 17 BSc3116 | 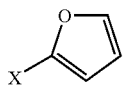 | H | H | 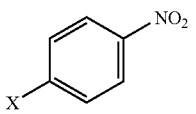 |
| Comp. 18 BSc3011 | 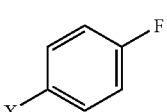 | H | H | 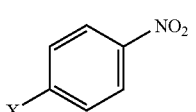 |
| Comp. 19 BSc2463 | 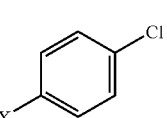 | H | H | 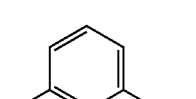 |
| Comp. 6 BSc3057 | 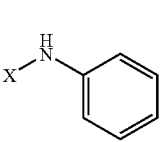 | H | H | 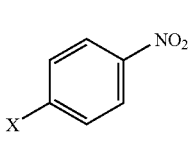 |
| Comp. 20 BSc3089 | 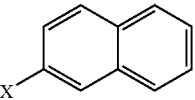 | H | H | 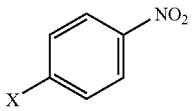 |
| Comp. 1 BSc2992 | 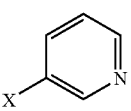 | H | H | 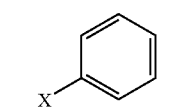 |

TABLE 1-continued

| Comap. 21 BSc2781 | 4-pyridyl | H | H | 4-bromophenyl |
| Comp. 2 BSc2993 | 3-pyridyl | H | H | coumarin-3-yl |
| Comp. 22 BSc2782 | thiophen-2-yl | H | H | phenyl |
| Comp. 23 BSc2785 | thiophen-2-yl | H | H | 3-methoxyphenyl |
| Comp. 24 BSc3015 | 4-fluoro-3-bromophenyl | H | H | phenyl |
| Comp. 25 BSc2755 | 2-chlorophenyl | H | H | 3-nitrophenyl |
| Comp. 5 BSc3010 | 4-fluorophenyl | H | H | coumarin-3-yl |
| Comp. 26 BSc2761 | 4-chlorophenyl | H | H | benzofuran-2-yl |
| Comp. 27 BSc2784 | 4-chlorophenyl | H | H | 3-methoxyphenyl |
| Comp. 28 BSc3091 | furan-2-yl | H | H | 4-bromophenyl |
| Comp. 29 BSc2780 | 4-chlorophenyl | H | H | thiophen-2-yl |
| Comp. 30 BSc3058 | phenylamino | H | H | 4-bromophenyl |
| Comp. 31 BSc2760 | 4-chlorophenyl | H | H | 4-fluorophenyl |

TABLE 1-continued
| | | | | |
|---|---|---|---|---|
| Comp. 32 BSc3052 | 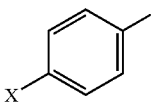 | H | H | 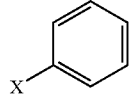 |
| Comp. 33 BSc3014 | 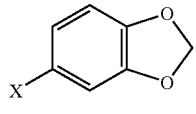 | H | H | 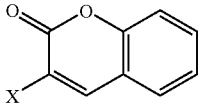 |
| Comp. 34 BSc2990 | 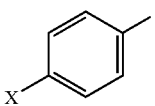 | H | H | 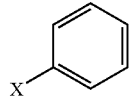 |
| Comp. 35 BSc2779 | 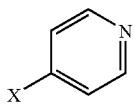 | H | H | 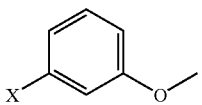 |
| Comp. 36 BSc3114 | 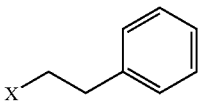 | H | H | 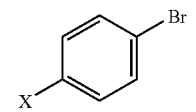 |
| Comp. 37 BSc2995 | 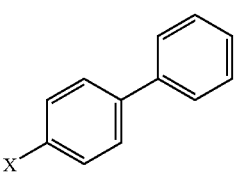 | H | H | 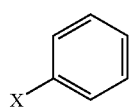 |
| Comp. 3 BSc3056 | 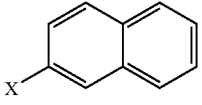 | H | H | 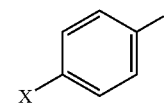 |
| Comp. 38 BSc3013 | 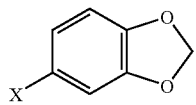 | H | H | 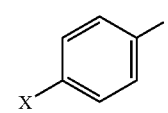 |
| Comp. 39 BSc2996 | 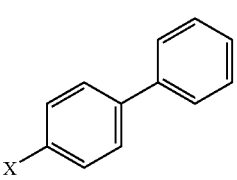 | H | H | 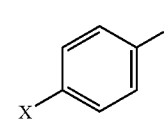 |
| Comp. 40 BSc3001 | 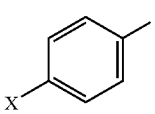 | H | H | 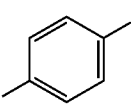 |
| Comp. 41 BSc3460 | 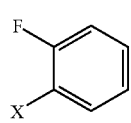 | H | H | 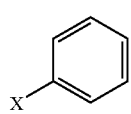 |
| Comp. 42 BSc3054 | 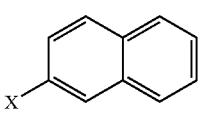 | H | H | 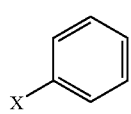 |

TABLE 1-continued
| | | | | |
|---|---|---|---|---|
| Comp. 43 BSc3090 | 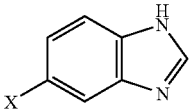 | H | H | 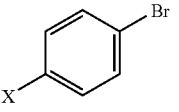 |
| Comp. 4 BSc3053 | 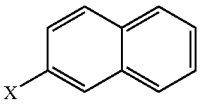 | H | H | 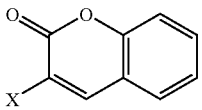 |
| Comp. 44 BSc3051 | 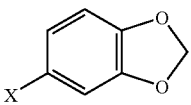 | H | H | 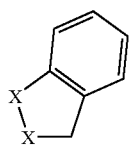 |
| Comp. 45 BSc3017 | 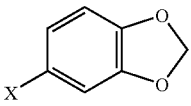 | H | H | 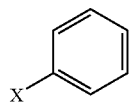 |
| Comp. 46 BSc2783 | 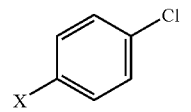 | H | H | 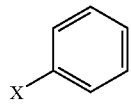 |
| Comp. 47 BSc2999 | 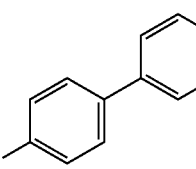 | H | H | 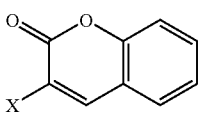 |
| Comp. 48 BSc2762 | 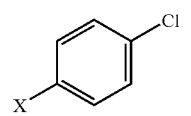 | H | H | 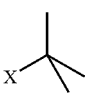 |
| Comp. 49 VD-1A | 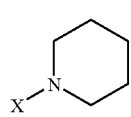 | H | H | 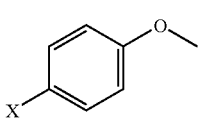 |
| Comp. 50 VD-108G | 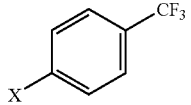 | H | H | 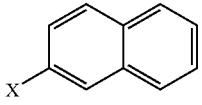 |
| Comp. 51 VD-100D | 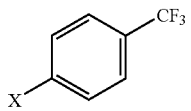 | H | H | 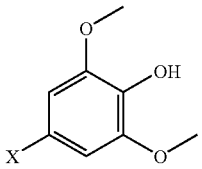 |
| Comp. 52 VD-108E | 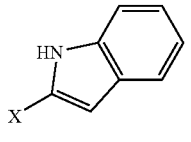 | H | H | 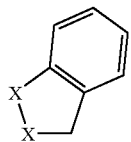 |

TABLE 1-continued

| Comp. 53 VD-108D | indole with X | H | H | 2,6-dimethoxy-4-X-phenol |
| Comp. 54 VD-108C | indole with X | H | H | adamantyl-X |
| Comp. 55 VD-108B | indole with X | H | H | 4-chlorophenyl-X |
| Comp. 56 VD-108A | indole with X | H | H | 4-isobutoxyphenyl-X |
| Comp. 57 VD-99E | indole with X | H | H | 4-cyanophenyl-X |
| Comp. 58 VD-99D | indole with X | H | H | 4-biphenyl-X |
| Comp. 59 VD-99C | indole with X | H | H | 2-naphthyl-X |
| Comp. 60 VD-99A | indole with X | H | H | 2-bromophenyl-X |
| Comp. 61 TSK125 | 4-biphenyl-X | H | H | 4-nitrophenyl-X |
| Comp. 62 TSK107 | benzimidazole with X | H | H | —$CH_3$ |

TABLE 1-continued
| | | | | |
|---|---|---|---|---|
| Comp. 63 TSK104 | 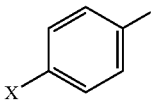 | H | H | —CH₃ |
| Comp. 64 TSK100 | 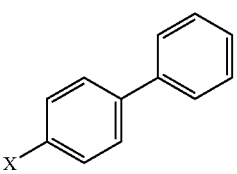 | H | H | —CH₃ |
| Comp. 65 VD-8H | 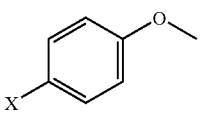 | H | H | 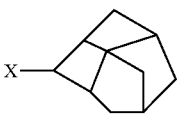 |
| Comp. 66 VD-7G | 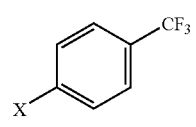 | H | H | 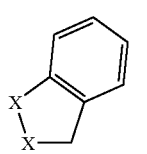 |
| Comp. 67 VD-3C | 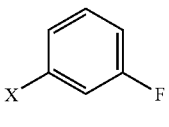 | H | H | 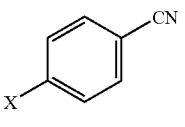 |
| Comp. 68 VD-2B | 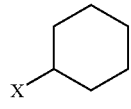 | H | H | 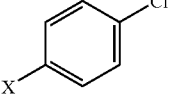 |
| Comp. 69 THY-1C | 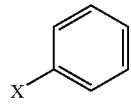 | H | H | 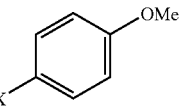 |
| Comp. 70 THY-2C | 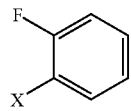 | H | H | 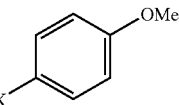 |
| Comp. 71 THY-1E | 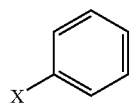 | H | H | 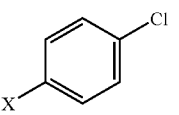 |
| Comp. 72 THY-2E | 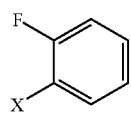 | H | H | 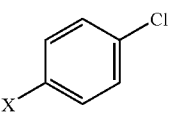 |
| Comp. 73 THY-2D | 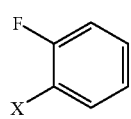 | H | H | 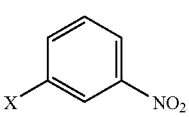 |
| Comp. 74 THY-2H | 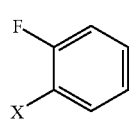 | H | H | 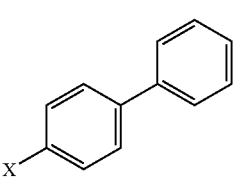 |

TABLE 1-continued

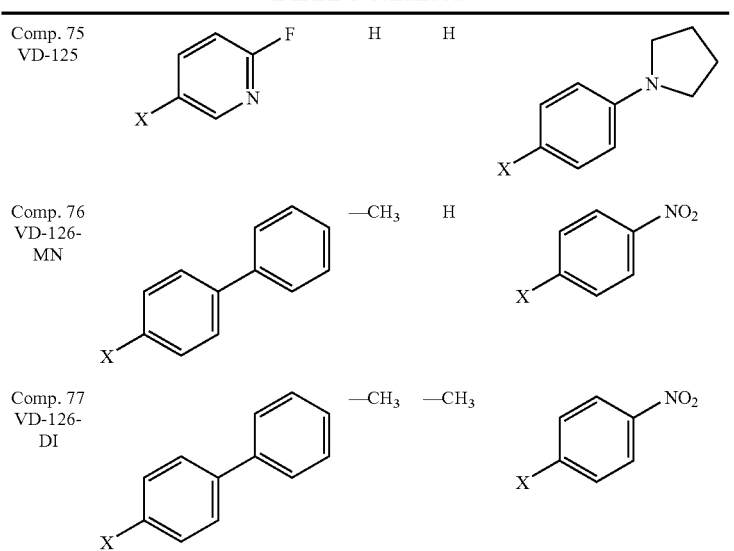

| | R5 | LDH (%) | ± | ID50 (μM) | DC50 (μM) | Inhibition in cells (%) | ± |
|---|---|---|---|---|---|---|---|
| Comp. 7 BSc2998 | H | 5.0 | 8.1 | 1.3 | 1.2 | 69.7 | 10.2 |
| Comp. 8 BSc3094 | H | 5.2 | 6.6 | 1.6 | 0.7 | 82.2 | 3.7 |
| Comp. 9 BSc3000 | H | 6.2 | 4.6 | 1.9 | 1.0 | 60.5 | 6.7 |
| Comp. 10 BSc3551 | H | 12.5 | 9.4 | 2.0 | 1.4 | 62.5 | 8.7 |
| Comp. 11 BSc2994 | H | 12.9 | 3.3 | 3.1 | 0.7 | N/D | N/D |
| Comp. 12 BSc2997 | H | 13.6 | 5.0 | 3.3 | 0.5 | N/D | N/D |
| Comp. 13 BSc3016 | H | 9.3 | 4.1 | 3.9 | 0.7 | 66.1 | 11.4 |
| Comp. 14 BSc3012 | H | 42.5 | 2.9 | 4.7 | 1.3 | N/D | N/D |
| Comp. 15 BSc2991 | H | −1.1 | 5.0 | 4.9 | 0.7 | N/D | N/D |
| Comp. 16 BSc3055 | H | 15.3 | 12.1 | 5.8 | 1.5 | N/D | N/D |
| Comp. 17 BSc3116 | H | 4.9 | 1.7 | 6.3 | 0.8 | N/D | N/D |
| Comp. 18 BSc3011 | H | 46.9 | 6.7 | 6.9 | 0.9 | N/D | N/D |
| Comp. 19 BSc2463 | —CH3 | 47.4 | 1.5 | 7.7 | 10.8 | N/D | N/D |
| Comp. 6 BSc3057 | H | 2.1 | 3.3 | 10.8 | 33.5 | N/D | N/D |
| Comp. 20 BSc3089 | H | 18.7 | 3.7 | 13.6 | 0.4 | N/D | N/D |
| Comp. 1 BSc2992 | H | 56.8 | 5.1 | 17.0 | 1.7 | N/D | N/D |
| Comp. 21 BSc2781 | H | 1.5 | 4.1 | 18.0 | 20.2 | N/D | N/D |
| Comp. 2 BSc2993 | H | 15.4 | 5.4 | 23.2 | 11.1 | N/D | N/D |
| Comp. 22 BSc2782 | H | 14.8 | 1.7 | 25.3 | 35.5 | N/D | N/D |
| Comp. 23 BSc2785 | H | 25.3 | 2.9 | 28.3 | >200 | N/D | N/D |
| Comp. 24 BSc3015 | H | 5.5 | 2.0 | 33.56 | 16.5 | N/D | N/D |
| Comp. 25 BSc2755 | H | 43.0 | 3.6 | 35.5 | >200 | N/D | N/D |
| Comp. 5 BSc3010 | H | 8.6 | 3.9 | 47.2 | >200 | N/D | N/D |
| Comp. 26 BSc2761 | H | −0.6 | 0.7 | 47.2 | 21.3 | N/D | N/D |
| Comp. 27 BSc2784 | H | 42.1 | 17.7 | 59.2 | >200 | N/D | N/D |

TABLE 1-continued

| | | | | | | | |
|---|---|---|---|---|---|---|---|
| Comp. 28 BSc3091 | H | 3.8 | 5.2 | 60.9 | 2.0 | N/D | N/D |
| Comp. 29 BSc2780 | H | 3.8 | 4.4 | 146.5 | >200 | N/D | N/D |
| Comp. 30 BSc3058 | H | 6.4 | 3.9 | 146.5 | >200 | N/D | N/D |
| Comp. 31 BSc2760 | H | 56.1 | 11.9 | 183.8 | >200 | N/D | N/D |
| Comp. 32 BSc3052 | —CH$_3$ | 18.4 | 10.2 | 194.5 | >200 | N/D | N/D |
| Comp. 33 BSc3014 | H | 2.0 | 1.4 | >200 | >200 | N/D | N/D |
| Comp. 34 BSc2990 | H | 2.6 | 1.3 | >200 | >200 | N/D | N/D |
| Comp. 35 BSc2779 | H | 3.2 | 4.5 | >200 | >200 | N/D | N/D |
| Comp. 36 BSc3114 | H | 3.3 | 4.5 | >200 | >200 | N/D | N/D |
| Comp. 37 BSc2995 | H | 3.6 | 4.5 | >200 | >200 | N/D | N/D |
| Comp. 3 BSc3056 | H | 4.2 | 1.8 | >200 | 168.7 | N/D | N/D |
| Comp. 38 BSc3013 | H | 4.6 | 5.2 | >200 | >200 | N/D | N/D |
| Comp. 39 BSc2996 | H | 4.9 | 5.8 | >200 | >200 | N/D | N/D |
| Comp. 40 BSc3001 | H | 4.9 | 4.9 | >200 | >200 | N/D | N/D |
| Comp. 41 BSc3460 | H | 6.5 | 4.5 | >200 | 127.1 | N/D | N/D |
| Comp. 42 BSc3054 | H | 8.2 | 5.1 | >200 | 16.4 | N/D | N/D |
| Comp. 43 BSc3090 | H | 11.5 | 8.7 | >200 | 31.7 | N/D | N/D |
| Comp. 4 BSc3053 | H | 15.7 | 9.7 | >200 | 88.0 | N/D | N/D |
| Comp. 44 BSc3051 | H | 18.8 | 7.7 | >200 | >200 | N/D | N/D |
| Comp. 45 BSc3017 | H | 22.6 | 8.7 | >200 | >200 | N/D | N/D |
| Comp. 46 BSc2783 | H | 34.3 | 4.9 | >200 | >200 | N/D | N/D |
| Comp. 47 BSc2999 | H | 44.7 | 9.6 | >200 | >200 | N/D | N/D |
| Comp. 48 BSc2762 | H | 48.1 | 2.4 | >200 | >200 | N/D | N/D |
| Comp. 49 VD-1A | H | −3.9 | 9.0 | >200 | >200 | Cytotoxic at 5 d | |
| Comp. 50 VD-108G | H | −7.6 | 1.0 | N/D | N/D | 52.6 | 10.4 |
| Comp. 51 VD-100D | H | −10.4 | 1.5 | 189.2 | >200 | 42.6 | 14.1 |
| Comp. 52 VD-108E | H | −9.6 | 5.7 | 49.4 | 89.1 | 53.2 | 6.7 |
| Comp. 53 VD-108D | H | −7.3 | 6.2 | 170.7 | >200 | 49.9 | 4.5 |
| Comp. 54 VD-108C | H | −2.1 | 5.7 | >200 | >200 | 56.6 | 4.6 |
| Comp. 55 VD-108B | H | −1.1 | 3.2 | 88.9 | 105.2 | 54.0 | 6.1 |
| Comp. 56 VD-108A | H | −0.6 | 2.9 | 110.5 | >200 | 50.8 | 3.4 |
| Comp. 57 VD-99E | H | 2.7 | 5.9 | >200 | >200 | 49.3 | 4.0 |
| Comp. 58 VD-99D | H | 54.5 | 2.3 | 98.9 | >200 | Cytotoxic at 5 d | |
| Comp. 59 VD-99C | H | 1.9 | 1.5 | 130.1 | 138.1 | Cytotoxic at 5 d | |
| Comp. 60 VD-99A | H | 0.1 | 6.4 | >200 | >200 | 41.5 | 7.3 |
| Comp. 61 TSK125 | —CH$_3$ | 16.6 | 2.7 | 9.8 | 13.6 | 62.6 | 11.5 |
| Comp. 62 TSK107 | 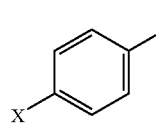 | −2.8 | 0.8 | 33.5 | 38.1 | 68.3 | 4.2 |

TABLE 1-continued

| Comp. | Structure | X | | | | | | |
|---|---|---|---|---|---|---|---|---|
| Comp. 63 TSK104 | 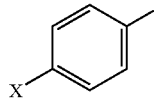 | Br | 1.2 | 1.9 | 13.6 | 15.9 | 50.0 | 11.0 |
| Comp. 64 TSK100 | 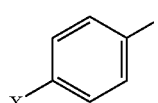 | Br | 8.9 | 6.8 | >200 | N/D | N/D | |
| Comp. 65 VD-8H | | H | 39.4 | 2.7 | 112.2 | >200 | 42.1 | 10.2 |
| Comp. 66 VD-7G | | H | -4.6 | 4.4 | 4.1 | 2.7 | 53.9 | 10.3 |
| Comp. 67 VD-3C | | H | 19.8 | 1.8 | 19.7 | 28.7 | Cytotoxic at 5 d | |
| Comp. 68 VD-2B | | H | -2.8 | 4.3 | 69.1 | 162.2 | 46.4 | 9.4 |
| Comp. 69 THY-1C | | H | N/D | N/D | 51.3 | 19.4 | N/D | N/D |
| Comp. 70 THY-2C | | H | N/D | N/D | 20.4 | 30.5 | N/D | N/D |
| Comp. 71 THY-1E | | H | N/D | N/D | >200 | >200 | N/D | N/D |
| Comp. 72 THY-2E | | H | N/D | N/D | 101.1 | >200 | N/D | N/D |
| Comp. 73 THY-2D | | H | N/D | N/D | 17.5 | 38.5 | N/D | N/D |
| Comp. 74 THY-2H | | H | N/D | N/D | 20.5 | 53.9 | N/D | N/D |
| Comp. 75 VD-125 | | H | 12.2 | 1.6 | 42.1 | 44.6 | N/D | N/D |
| Comp. 76 VD-126-MN | | H | N/D | N/D | 67.6 | 138.2 | N/D | N/D |
| Comp. 77 VD-126-DI | | H | N/D | N/D | 10.9 | 17.7 | N/D | N/D |

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. A method of treatment of neurodegenerative diseases, disorders or conditions related to tau protein aggregation comprising administering to a subject an effective amount of a compound having the formula (I), wherein the compound is an inhibitor of tau aggregation:

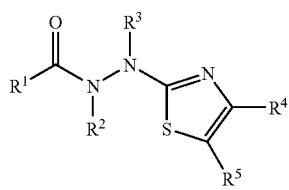

wherein $R^1$ represents —$R^6$, $R^4$ represents

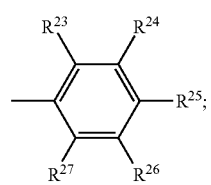

$R^5$ represents —H or —$CR^{15}R^{16}R^{17}$;

$R^6$ represents

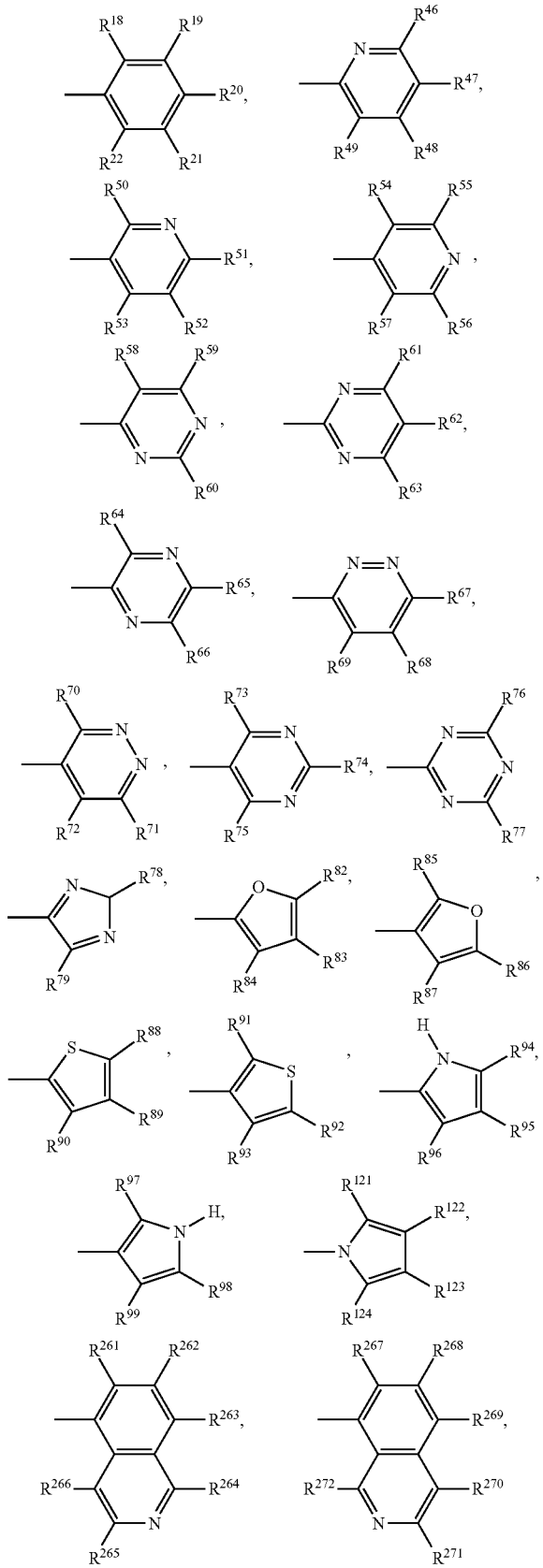

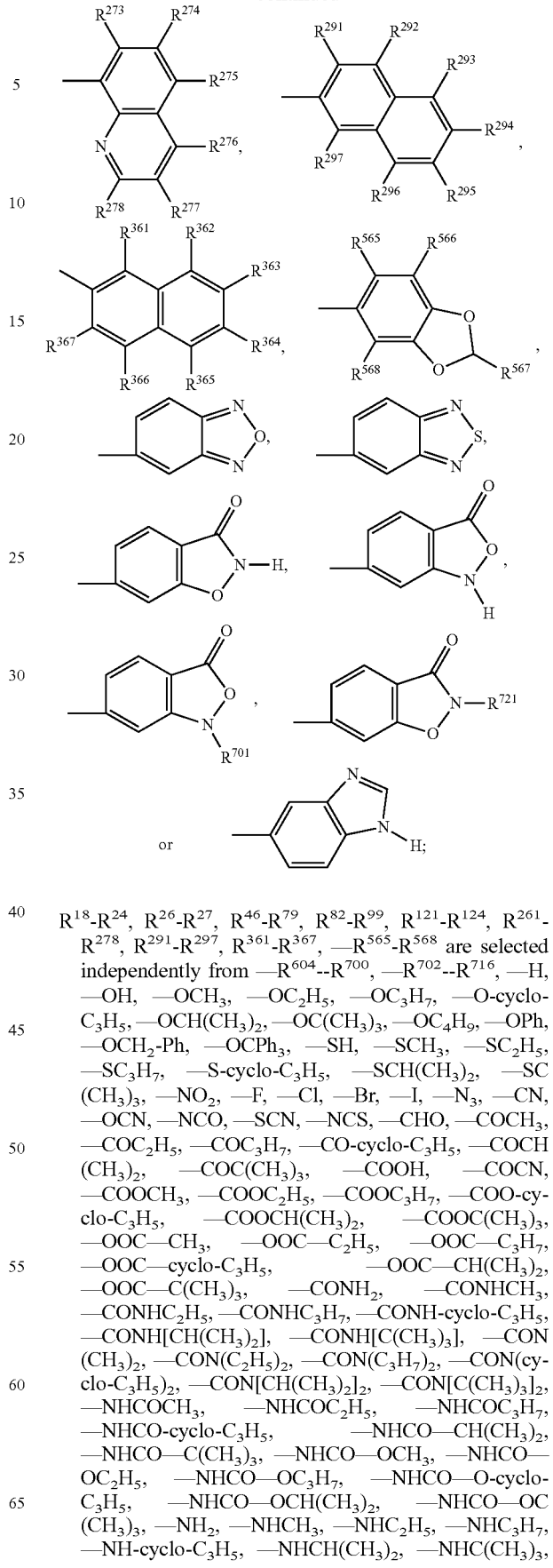

$R^{18}$-$R^{24}$, $R^{26}$-$R^{27}$, $R^{46}$-$R^{79}$, $R^{82}$-$R^{99}$, $R^{121}$-$R^{124}$, $R^{261}$-$R^{278}$, $R^{291}$-$R^{297}$, $R^{361}$-$R^{367}$, —$R^{565}$-$R^{568}$ are selected independently from —$R^{604}$--$R^{700}$, —$R^{702}$--$R^{716}$, —H, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OPh, —OCH$_2$-Ph, —OCPh$_3$, —SH, —SCH$_3$, —SC$_2$H$_5$, —SC$_3$H$_7$, —S-cyclo-C$_3$H$_5$, —SCH(CH$_3$)$_2$, —SC(CH$_3$)$_3$, —NO$_2$, —F, —Cl, —Br, —I, —N$_3$, —CN, —OCN, —NCO, —SCN, —NCS, —CHO, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, —COCN, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —OOC—CH$_3$, —OOC—C$_2$H$_5$, —OOC—C$_3$H$_7$, —OOC—cyclo-C$_3$H$_5$, —OOC—CH(CH$_3$)$_2$, —OOC—C(CH$_3$)$_3$, —CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON(cyclo-C$_3$H$_5$)$_2$, —CON[CH(CH$_3$)$_2$]$_2$, —CON[C(CH$_3$)$_3$]$_2$, —NHCOCH$_3$, —NHCOC$_2$H$_5$, —NHCOC$_3$H$_7$, —NHCO-cyclo-C$_3$H$_5$, —NHCO—CH(CH$_3$)$_2$, —NHCO—C(CH$_3$)$_3$, —NHCO—OCH$_3$, —NHCO—OC$_2$H$_5$, —NHCO—OC$_3$H$_7$, —NHCO—O-cyclo-C$_3$H$_5$, —NHCO—OCH(CH$_3$)$_2$, —NHCO—OC(CH$_3$)$_3$, —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH₃)₂, —N(C₂H₅)₂, —N(C₃H₇)₂, —N(cyclo-C₃H₅)₂, —N[CH(CH₃)₂]₂, —N[C(CH₃)₃]₂, —SOCH₃, —SOC₂H₅, —SOC₃H₇, —SO-cyclo-C₃H₅, —SOCH(CH₃)₂, —SOC(CH₃)₃, —SO₂CH₃, —SO₂C₂H₅, —SO₂C₃H₇, —SO₂-cyclo-C₃H₅, —SO₂CH(CH₃)₂, —SO₂C(CH₃)₃, —SO₃H, —SO₃CH₃, —SO₃C₂H₅, —SO₃C₃H₇, —SO₃-cyclo-C₃H₅, —SO₃CH(CH₃)₂, —SO₃C(CH₃)₃, —SO₂NH₂, —OCF₃, —OC₂F₅, —O—COOCH₃, —O—COOC₂H₅, —O—COOC₃H₇, —O—COO-cyclo-C₃H₅, —O—COOCH(CH₃)₂, —O—COOC(CH₃)₃, —NH—CO—NH₂, —NH—CO—NHCH₃, —NH—CO—NHC₂H₅, —NH—CO—NHC₃H₇, —NH—CO—NH-cyclo-C₃H₅, —NH—CO—NH[CH(CH₃)₂], —NH—CO—NH[C(CH₃)₃], —NH—CO—N(CH₃)₂, —NH—CO—N(C₂H₅)₂, —NH—CO—N(C₃H₇)₂, —NH—CO—N(cyclo-C₃H₅)₂, —NH—CO—N[CH(CH₃)₂]₂, —NH—CO—N[C(CH₃)₃]₂, —NH—CS—NH₂, —NH—CS—NHCH₃, —NH—CS—NHC₂H₅, —NH—CS—NHC₃H₇, —NH—CS—NH-cyclo-C₃H₅, —NH—CS—NH[CH(CH₃)₂], —NH—CS—NH[C(CH₃)₃], —NH—CS—N(CH₃)₂, —NH—CS—N(C₂H₅)₂, —NH—CS—N(C₃H₇)₂, —NH—CS—N(cyclo-C₃H₅)₂, —NH—CS—N[CH(CH₃)₂]₂, —NH—CS—N[C(CH₃)₃]₂, —NH—C(=NH)—NH₂, —NH—C(=NH)—NHCH₃, —NH—C(=NH)—NHC₂H₅, —NH—C(=NH)—NHC₃H₇, —NH—C(=NH)—NH-cyclo-C₃H₅, —NH—C(=NH)—NH[CH(CH₃)₂], —NH—C(=NH)—NH[C(CH₃)₃], —NH—C(=NH)—N(CH₃)₂, —NH—C(=NH)—N(C₂H₅)₂, —NH—C(=NH)—N(C₃H₇)₂, —NH—C(=NH)—N(cyclo-C₃H₅)₂, —NH—C(=NH)—N[CH(CH₃)₂]₂, —NH—C(=NH)—N[C(CH₃)₃]₂, —O—CO—NH₂, —O—CO—NHCH₃, —O—CO—NHC₂H₅, —O—CO—NHC₃H₇, —O—CO—NH-cyclo-C₃H₅, —O—CO—NH[CH(CH₃)₂], —O—CO—NH[C(CH₃)₃], —O—CO—N(CH₃)₂, —O—CO—N(C₂H₅)₂, —O—CO—N(C₃H₇)₂, —O—CO—N(cyclo-C₃H₅)₂, —O—CO—N[CH(CH₃)₂]₂, —O—CO—N[C(CH₃)₃]₂, —O—CO—OCH₃, —O—CO--OC₂H₅, —O—CO—OC₃H₇, —O—CO—O-cyclo-C₃H₅, —O—CO—OCH(CH₃)₂, or —O—CO—OC(CH₃)₃;

$R^2$, $R^3$, $R^{15}$, $R^{16}$, $R^{17}$ represent —H;

$R^{25}$ represents —NO₂;

$R^{604}$ to $R^{716}$ and $R^{721}$ represent

H, —CH₃, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, cyclo-C₃H₅, cyclo-C₄H₇, cyclo-C₅H₉, cyclo-C₆H₁₁, cyclo-C₇H₁₃, cyclo-C₈H₁₅, -Ph, —CH₂-Ph, —CPh₃, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₇H₁₅, —C₈H₁₇, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH=CH₂, —CH₂—CH=CH₂, —C(CH₃)=CH₂, —CH=CH—CH₃, —C₂H₄—CH=CH₂, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—CH=C(CH₃)₂, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH=C(CH₃)—C₂H₅, —CH=CH—CH(CH₃)₂, —CH₂—CH=CH—CH₂—CH₃, —CH=CH—CH₂—CH=CH₂, —C(CH₃)=CH—CH=CH₂, —CH=C(CH₃)—CH=CH₂, (CH₃)—CH=CH—CH₃, —CH=CH—CH(CH₃)₂, —CH=C(CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, —C(CH₃)=CH—CH=CH₂, —CH=CH—C(CH₃)=CH₂, —C₄H₈—CH=CH₂, —C₃H₆—CH=CH—CH₃, —C₂H₄—CH=CH—C₂H₅, —CH₂—CH=CH—C₃H₇, —CH=CH—C₄H₉, —C₃H₆—C(CH₃)=CH₂, —C₂H₄—CH(CH₃)—CH=CH₂, —CH₂—CH(CH₃)—CH₂—CH=CH₂, —C₂H₄—CH=C(CH₃)₂, —CH(CH₃)—C₂H₄—CH=CH₂, —CH₂—CH(C≡H)₂, —C₂H₄—C(CH₃)=CH—CH₃, —CH₂—CH(CH₃)—CH=CH—CH₃, —C≡C—C≡CH, —CH(CH₃)—CH₂—CH=CH—CH₃, —CH₂—CH=CH—CH(CH₃)₂, —CH₂—CH=C(CH₃)—C₂H₅, —CH₂—C(CH₃)=CH—C₂H₅, —CH(CH₃)—CH=CH—C₂H₅, —CH=CH—CH₂—CH(CH₃)₂, —CH=CH—CH(CH₃)—C₂H₅, —CH=C(CH₃)—C₃H₇, —C(CH₃)=CH—C₃H₇, —CH₂—CH(CH₃)—C(CH₃)=CH₂, —C[C(CH₃)₃]=CH₂, —CH(CH₃)—C≡C—C≡CH, —CH(CH₃)—CH₂—C(CH₃)=CH₂, —CH(CH₃)—CH(CH₃)—CH=CH₂, —CH₂—C≡C—C≡H, —CH=CH—C₂H₄—CH=CH₂, —CH₂—C(CH₃)₂—CH=CH₂, —C(CH₃)₂—CH₂—CH=CH₂, —CH₂—C(CH₃)=C(CH₃)₂, —CH(CH₃)—CH=C(CH₃)₂, —C(CH₃)₂—CH=CH—CH₃, —CH=CH—CH₂—CH=CH—CH₃, —CH(CH₃)—C(CH₃)=CH—CH₃, —C≡C—C≡C—CH₃, —CH=C(CH₃)—CH(CH₃)₂, —C(CH₃)=CH—CH(CH₃)₂, —CH(C≡CH)C≡C—CH₃, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)—CH=CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —CH(C≡CH)₂, —C(C₂H₅)=CH—C₂H₅, —C(C₂H₅)=C(CH₃)₂, —C[CH(CH₃)(C₂H₅)]=CH₂, —C[CH₂—CH(CH₃)₂]=CH₂, —C₂H₄—CH=CH—CH=CH₂, —CH₂—CH=CH—CH₂—CH=CH₂, —C₃H₆—C≡C—CH₃, —CH₂—CH=CH—CH=CH—CH₃, —CH=CH—CH=CH—C₂H₅, —CH=CH-Ph, —CH₂—CH=CH—C(CH₃)=CH₂, —CH₂—CH=C(CH₃)—CH=CH₂, —C≡C—C≡C—C₂H₅, —CH₂—C(CH₃)=CH—CH=CH₂, —CH(CH₃)—CH₂—C≡CH, —CH₂—C≡C—CH₂—C≡CH, —CH(CH₃)—CH=CH—CH=CH₂, —CH=CH—CH₂—C(CH₃)=CH₂, —CH(CH₃)—C≡C—CH₃, —CH=CH—CH=C(CH₃)—CH=CH₂, —CH=C(CH₃)—CH₂—CH=CH₂, —C≡C—C₂H₄—C≡CH, —C₂H₄—CH(CH₃)—C≡CH, —C(CH₃)=CH—CH₂—CH=CH₂, —C≡C—CH(CH₃)—C≡CH, —CH=CH—CH=C(CH₃)₂, —CH₂—CH(CH₃)—CH₂—C≡CH, —C(C≡CH)₂—CH₃, —CH=C(CH₃)—CH=CH—CH₃, —CH=C(CH₃)—CH=CH—CH₃, —CH(C≡CH)—CH₂—C≡CH, —C(CH₃)=CH—CH=CH—CH₃, —C₂H₄—C≡C—C≡CH, —CH=C(CH₃)—C(CH₃)

=CH$_2$, —C(CH$_3$)=CH—C(CH$_3$)=CH$_2$, —C≡C—CH$_2$—C≡C—CH$_3$, —C(CH$_3$)=C(CH$_3$)—CH=CH$_2$, —CH=CH—CH=CH—CH=CH$_2$, —C≡CH, —C≡C—CH$_3$, —CH$_2$—C≡CH, —C$_2$H$_4$—C≡CH, —CH(C$_3$H$_7$)—C≡CH, —CH$_2$—C≡C—CH$_3$, —C≡C—C$_2$H$_5$, —C$_3$H$_6$—C≡CH, —C$_2$H$_4$—C≡C—CH$_3$, —CH$_2$—C≡C—C$_2$H$_5$, —C≡C—C$_3$H$_7$, —CH(CH$_3$)—C≡CH, —C$_4$H$_8$—C≡CH, —C$_2$H$_4$—C≡C—C$_2$H$_5$, —CH$_2$—C≡C—C$_3$H$_7$, —C≡C—C$_4$H$_9$, —C≡C—C(CH$_3$)$_3$, —CH(CH$_3$)—C$_2$H$_4$—C≡CH, —CH$_2$—CH(CH$_3$)—C≡C—CH$_3$, —CH(CH$_3$)—CH$_2$—C≡C—CH$_3$, —CH(CH$_3$)—C≡C—C$_2$H$_5$, —CH$_2$—C≡C—CH(CH$_3$)$_2$, —C≡C—CH(CH$_3$)—C$_2$H$_5$, —C≡C—CH$_2$—CH(CH$_3$)$_2$, —CH(C$_2$H$_5$)—C≡C—CH$_3$, —C(CH$_3$)$_2$—C≡C—CH$_3$, —CH(C$_2$H$_5$)—CH$_2$—C≡CH, —CH$_2$—CH(C$_2$H$_5$)—C≡CH, —C(CH$_3$)$_2$—CH$_2$—C≡CH, —CH$_2$—C≡C—C≡C—CH$_3$, —CH$_2$—C(CH$_3$)$_2$—C≡CH, —CH(CH$_3$)—CH(CH$_3$)—C≡CH, —C(CH$_3$)(C$_2$H$_5$)—C≡CH, -Ph, or —CH$_2$-Ph, and enantiomers, stereoisomeric forms, mixtures of enantiomers, diastereomers, mixtures of diastereomers, tautomers, and racemates of the above mentioned compounds and pharmaceutically acceptable salts thereof.

2. The method of claim 1, wherein the neurodegenerative disease, disorder or condition related to tau protein aggregation is selected from the group consisting of Alzheimer Disease and progressive supranuclear palsy (PSP).

3. The method of claim 1, wherein administering to a subject an effective amount of a compound having the formula (I) comprises administering a compound having the following formula (I):

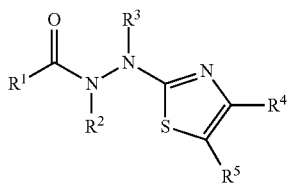

wherein R$^5$ represents —H.

4. The method of claim 1, wherein administering to a subject an effective amount of a compound having the formula (I) comprises administering a compound having the following formula (II):

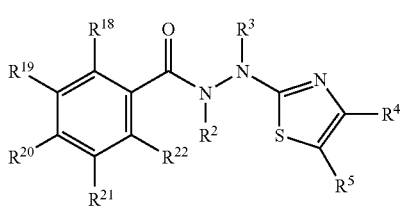

wherein R$^2$-R$^5$ and R$^{18}$-R$^{22}$ have the meanings as defined in claim 1.

5. The method of claim 1, wherein administering to a subject an effective amount of a compound having the formula (I) comprises administering a compound having the following formula (IV):

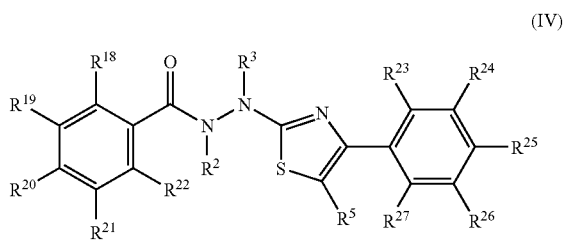

wherein

R$^5$ represents —H, and

R$^2$, R$^3$, and R$^{18}$-R$^{27}$ have the meanings as defined in claim 1.

6. The method of claim 1, wherein administering to a subject an effective amount of a compound having the formula (I) comprises administering one or more of the following compounds:

N'-[4-(4-nitrophenyl)-1,3-thiazol-2-yl]-1,1'-biphenyl-4-carbohydrazide (Compound 7), N'-[4-(4-Nitrophenyl)-1,3-thiazol-2-yl]-1H-benzimidazole-5-carbohydrazide (Compound 8), N'-[4-(4-nitrophenyl)-1,3-thiazol-2-yl]nicotinohydrazide (Compound 11), N'-[4-(4-nitrophenyl)-1,3-thiazol-2-yl]-1,3-benzodioxole-5-carbohydrazide (Compound 13), N'-[4-(4-nitrophenyl)-1,3-thiazol-2-yl]-2-furohydrazide (Compound 17), 4-fluoro-N'-[4-(4-nitrophenyl)-1,3-thiazol-2-yl]benzohydrazide (Compound 18), N'-(4-(4-Nitrophenyl)thiazol-2-yl)-2-naphthohydrazide (Compound 20) and N'-[5-methyl-4-(4-nitrophenyl)-1,3-thiazol-2-yl]-1,1'-biphenyl-4-carbohydrazide (Compound 61).

* * * * *